(12) United States Patent
Wang et al.

(10) Patent No.: US 7,615,680 B2
(45) Date of Patent: Nov. 10, 2009

(54) TEMPORAL SEED PROMOTERS FOR EXPRESSING GENES IN PLANTS

(75) Inventors: Qi Wang, St. Louis, MO (US); Lisa M. Weaver, O'Fallon, MO (US); Tim N. Oulmassov, Chesterfield, MO (US); Jeffrey Ahrens, Manchester, MO (US); Patrice Dubois, Richmond Heights, MO (US); Jeffery Q. Shen, Henderson, NV (US)

(73) Assignee: Monsanto Technology LLC, St. Louis, MO (US)

( * ) Notice: Subject to any disclaimer, the term of this patent is extended or adjusted under 35 U.S.C. 154(b) by 151 days.

(21) Appl. No.: 11/625,709

(22) Filed: Jan. 22, 2007

(65) Prior Publication Data

US 2007/0180570 A1  Aug. 2, 2007

Related U.S. Application Data

(63) Continuation of application No. 10/429,555, filed on May 5, 2003, now Pat. No. 7,179,959.

(60) Provisional application No. 60/377,247, filed on May 3, 2002.

(51) Int. Cl.
| | |
|---|---|
| C12N 15/29 | (2006.01) |
| C12N 15/63 | (2006.01) |
| C12N 15/82 | (2006.01) |
| A01H 5/00 | (2006.01) |
| A01H 5/10 | (2006.01) |

(52) U.S. Cl. ............... 800/287; 800/284; 800/286; 800/294; 800/298; 800/312; 536/23.1; 536/24.1; 435/320.1; 435/419

(58) Field of Classification Search ............ None
See application file for complete search history.

(56) References Cited

U.S. PATENT DOCUMENTS 5,981,841 A  11/1999  Santino et al. ............. 800/298
6,127,600 A  10/2000  Beach et al. ............. 800/278
6,198,021 B1  3/2001  Lange et al. ............. 800/278
6,288,304 B1  9/2001  Moloney et al. .......... 800/288

FOREIGN PATENT DOCUMENTS

| EP | 1 050 585 | 11/2000 |
| WO | WO 99/03983 | 1/1999 |
| WO | WO 99/64579 | 12/1999 |
| WO | WO 01/11061 | 2/2001 |
| WO | WO 01/16340 | 3/2001 |
| WO | WO 02/090497 | 11/2002 |

OTHER PUBLICATIONS

GenBank Accession M97285.*
Lee, P.F. et al. Botanical Bulletin of Academia Sinica (Taipei), (Jul. 2000) vol. 41, No. 3, pp. 175-182.*
Calvo et al., "Cloning, mapping, and analysis of expression of the Em-like gene family in soybean," *Theor Appl Genet*, 94:957-967, 1997.
Database accession No. GMAF4805, Jan. 19, 1997.
Database accession No. GMU66317, Jul. 24, 1997.
GenBank Database accession No. K00821, Apr. 27, 1993.
GenBank Database accession No. M97285, Apr. 27, 1993.
GenBank Database accession No. Y12089, Mar. 19, 1998.
Haslekas et al., "The expression of a peroxiredoxin antioxidant gene, AtPer1, in *Arabidopsis thaliana* is seed specific and related to dormancy," *Plant Molecular Biology*, 36:833-845, 1998.
Lee et al., "Genomic nucleotide sequence of a soybean seed maturation protein GmPM9 gene," *Plant Physiol.*, 100:2121-2122, 1992.
Vodkin et al., "cA lectin gene insertion has the structural features of a transposable element," *Cell*, 34:1023-1031, 1983.

* cited by examiner

*Primary Examiner*—Russell Kallis
(74) *Attorney, Agent, or Firm*—Erin Robert, Esq.; Sonnenschein Nath & Rosenthal LLP

(57) ABSTRACT

The present invention relates to the field of plant genetic engineering. More specifically, the present invention relates to seed specific gene expression during a defined period of embryogenesis. The present invention provides promoters capable of transcribing heterologous nucleic acid sequences in seeds, and methods of modifying, producing, and using the same.

27 Claims, 13 Drawing Sheets

TEMPORAL SEED PROMOTERS FOR EXPRESSING GENES IN PLANTS

This application is a continuation application of application Ser. No. 10/429,555, filed May 5, 2003 now U.S. Pat. No. 7,179,959, which claims the benefit of the filing date of the provisional Application U.S. Ser. No. 60/377,247, filed May 3, 2002, the entire disclosures of which are specifically incorporated herein by reference.

The present invention relates to the field of plant genetic engineering. More specifically, the present invention relates to seed specific gene expression with certain temporal profiles during embryogenesis. The invention provides promoters capable of transcribing heterologous nucleic acid sequences in seeds, and methods of modifying, producing, and using the same.

Seeds provide and important source of dietary protein for humans and livestock. However, the nutritional content of seeds is often inadequate. For example, many seed proteins are deficient in one or more essential amino acids. This deficiency may be overcome by genetically modifying the native or non-native proteins to have a more nutritionally complete composition of amino acids (or some other desirable feature) and to overexpress the modified proteins in the transgenic plants. Alternatively, one or more genes could be introduced into a crop plant to manipulate the metabolic pathways and modify the free amino acid content. These approaches are useful in producing crops exhibiting improved agronomic (e.g., yield), nutritional, and pharmaceutical properties.

Introduction of a gene can cause deleterious effects on plant growth and development. Under such circumstances, the expression of the gene may need to be limited to the desired target tissue. For example, it might be necessary to express an amino acid deregulation gene in a seed-specific or seed-enhanced fashion to avoid an undesired phenotype that may affect yield or other agronomic traits. In other cases, expression of the transgene needs to be further limited within a defined period of time during the growth and development (temporal profile) of the specific target tissue. For example, it might be necessary to express a fatty acid metabolic gene during the time when oil biosynthesis is most active in seed.

The promoter portion of a gene plays a central role in controlling gene expression. Along the promoter region, the transcription machinery is assembled and transcription is initiated. This early step is often a key regulatory step relative to subsequent stages of gene expression. Transcription initiation at the promoter may be regulated in several ways. For example, a promoter may be induced by the presence of a particular compound, express a gene only in a specific tissue, or constitutively express a coding sequence. Thus, transcription of a coding sequence may be modified by operably linking the coding sequence to promoters with different regulatory characteristics, the availability of which is a problem addressed by this disclosure.

SUMMARY OF THE INVENTION

The present invention includes and provides a substantially purified nucleic acid molecule encoding a nucleic acid sequence having at least 75% identity to SEQ ID NO: 1 or its complement.

The present invention includes and provides a plant comprising an introduced nucleic acid molecule that comprises a promoter comprising a nucleic acid sequence having at least 75% identity to SEQ ID NO: 1 or its complement.

The present invention includes and provides a plant comprising an introduced nucleic acid molecule that comprises a promoter comprising a nucleic acid sequence selected from the group consisting of SEQ ID NOs: 1-4 and complements thereof.

The present invention includes and provides a method of producing a transformed plant comprising: providing a nucleic acid molecule that comprises a promoter comprising a nucleic acid sequence selected from the group consisting of SEQ ID NOs: 1-4 and complements thereof, operably linked to a structural nucleic acid sequence; and, transforming a plant with said nucleic acid molecule.

The present invention includes and provides a method of expressing a structural nucleic acid molecule in a seed comprising: growing a plant containing an introduced nucleic acid molecule that comprises a promoter comprising a nucleic acid sequence selected from the group consisting of SEQ ID NOs: 1-4 and complements thereof, operably linked to said structural nucleic acid molecule, wherein said plant produces said seed and said structural nucleic acid molecule is transcribed in said seed; and, isolating said seed.

The present invention includes and provides a method of obtaining a seed enhanced in a product of a structural nucleic acid molecule comprising: growing a plant containing an introduced nucleic acid molecule that comprises a promoter comprising a nucleic acid sequence selected from the group consisting of SEQ ID NOs: 1-4 and complements thereof, operably linked to said structural nucleic acid molecule, wherein said transformed plant produces said seed and said structural nucleic acid molecule is transcribed in said seed; and, isolating said seed from said plant.

The present invention includes and provides a method of obtaining meal enhanced in a product of a structural nucleic acid molecule comprising: growing a plant containing an introduced nucleic acid molecule that comprises a promoter comprising a nucleic acid sequence selected from the group consisting of SEQ ID NOs: 1-4 and complements thereof, operably linked to said structural nucleic acid molecule, wherein said plant produces a seed and said structural nucleic acid molecule is transcribed in said seed; and, preparing said meal comprising said plant or part thereof.

The present invention includes and provides a method of obtaining feedstock enhanced in a product of a structural nucleic acid molecule comprising: growing a plant containing an introduced nucleic acid molecule that comprises a promoter comprising a nucleic acid sequence selected from the group consisting of SEQ ID NOs: 1-4 and complements thereof, operably linked to said structural nucleic acid molecule, wherein said plant produces a seed and said structural nucleic acid molecule is transcribed in said seed; and, preparing said feedstock comprising said plant or part thereof.

The present invention includes and provides a method of obtaining oil enhanced in a product of a structural nucleic acid molecule comprising: growing a plant containing an introduced nucleic acid molecule that comprises a promoter comprising a nucleic acid sequence that hybridizes under stringent conditions with a nucleic acid sequence selected from the group consisting of SEQ ID NOs: 1-4 and complements thereof, operably linked to said structural nucleic acid molecule, wherein said plant produces a seed and said structural nucleic acid molecule is transcribed in said seed; and, isolating said oil.

The present invention includes and provides a cell containing a vector comprising a nucleic acid sequence selected from the group consisting of SEQ ID NOs: 1-4 and complements thereof.

The present invention includes and provides oil produced from one or more seeds of a plant containing an introduced nucleic acid molecule that comprises a promoter comprising a nucleic acid sequence selected from the group consisting of SEQ ID NOs: 1-4 and complements thereof.

The present invention includes and provides oil produced from one or more seeds of a plant containing an introduced nucleic acid molecule that comprises a promoter comprising a nucleic acid sequence selected from the group consisting of SEQ ID NOs: 1-4 and complements thereof, operably linked to a structural nucleic acid sequence, wherein the promoter is heterologous with respect to the structural nucleic acid sequence.

The present invention includes and provides a seed generated by a plant containing an introduced nucleic acid molecule that comprises: a promoter comprising a nucleic acid sequence selected from the group consisting of SEQ ID NOs: 1-4 and complements thereof.

The present invention includes and provides feedstock comprising a plant or part thereof containing an introduced nucleic acid molecule that comprises a promoter comprising a nucleic acid sequence selected from the group consisting of SEQ ID NOs: 1-4 and complements thereof.

The present invention includes and provides meal comprising plant material from a plant containing an introduced nucleic acid molecule that comprises a promoter comprising a nucleic acid sequence selected from the group consisting of SEQ ID NOs: 1-4 and complements thereof.

The present invention includes and provides a container of seeds, wherein at least 25% of said seeds comprises a promoter comprising a nucleic acid sequence selected from the group consisting of SEQ ID NOs: 1-4 and complements thereof, operably linked to a structural nucleic acid sequence, wherein said promoter is heterologous with respect to the structural nucleic acid sequence.

The present invention includes and provides a method for expressing a structural nucleic acid sequence in a plant, comprising: transforming said plant with a nucleic acid molecule comprising a promoter operably linked to said structural nucleic acid sequence, wherein said promoter comprises a sequence selected from the group consisting of SEQ ID NOs: 1-4 and complements thereof, and wherein said promoter and said structural nucleic acid sequence are heterologous with respect to each other, and; growing said plant.

The present invention includes and provides a method of accumulating free amino acids in a the seed of a plant, comprising: transforming said plant with a nucleic acid molecule comprising a promoter operably linked to a structural nucleic acid sequence encoding an amino acid biosynthesis gene, wherein said promoter comprises a sequence selected from the group consisting of SEQ ID NOs: 1-4 and complements thereof, and wherein said promoter and said structural nucleic acid sequence are heterologous with respect to each other, and; growing said plant.

The present invention includes and provides a method for regulating the germination of a soybean seed, comprising transforming a plant with a nucleic acid molecule comprising a promoter operably linked to a structural nucleic acid sequence encoding a gibberellin biosynthetic polypeptide, wherein said promoter comprises a sequence selected from the group consisting of SEQ ID NOs: 1-4 and complements thereof, and wherein said promoter and said structural nucleic acid sequence are heterologous with respect to each other; growing said plant; harvesting seed from said plant; and, planting said seed.

BRIEF DESCRIPTION OF THE SEQUENCES

Figure 1:
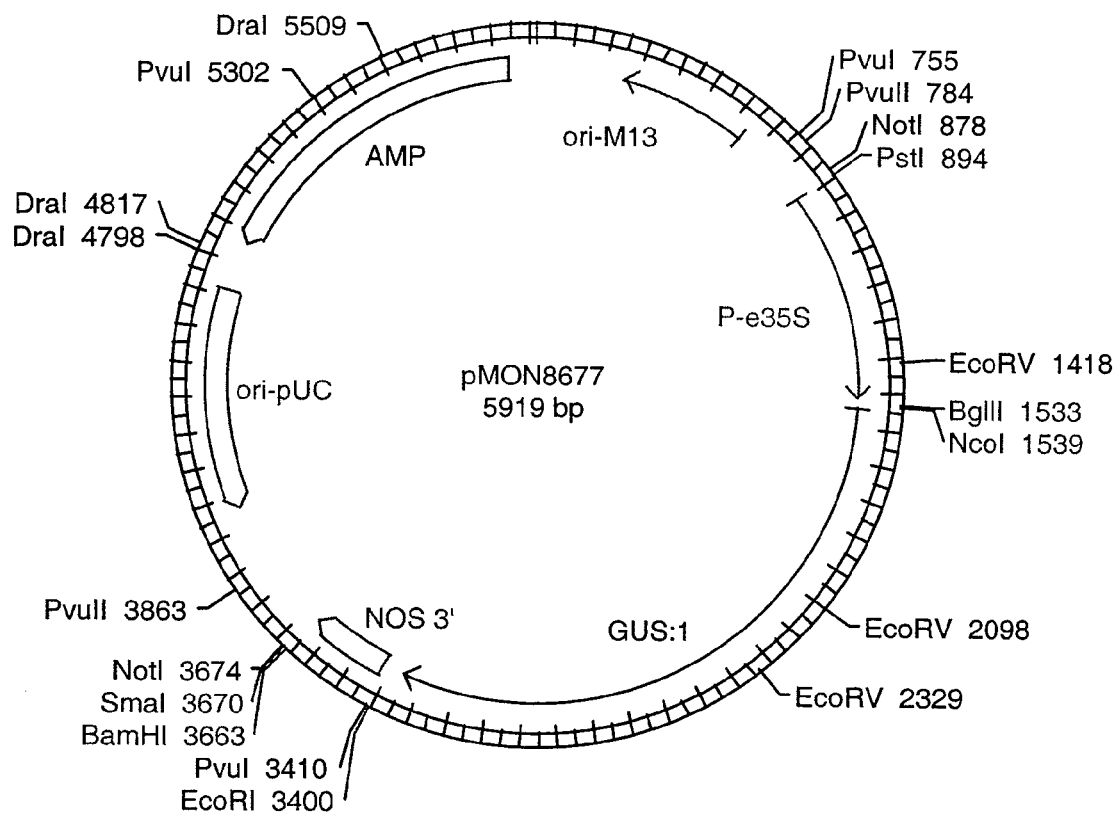
FIG. 1 is a schematic representation of pMON8677.

SEQ ID NO: 1 represents a sle2 gene promoter.
SEQ ID NO: 2 represents a lea9 promoter.
SEQ ID NO: 3 represents an AtPer1 promoter.
SEQ ID NO: 4 represents a lectin promoter.
SEQ ID NOs: 5 to 25 represent primer sequences.

Definitions

The following definitions are provided as an aid to understanding the detailed description of the present invention.

The phrases "coding sequence," "structural sequence," and "structural nucleic acid sequence" refer to a physical structure comprising an orderly arrangement of nucleotides. The nucleotides are arranged in a series of triplets that each form a codon. Each codon encodes a specific amino acid. Thus, the coding sequence, structural sequence, and structural nucleic acid sequence encode a series of amino acids forming a protein, polypeptide, or peptide sequence. The coding sequence, structural sequence, and structural nucleic acid sequence may be contained within a larger nucleic acid molecule, vector, or the like. In addition, the orderly arrangement of nucleotides in these sequences may be depicted in the form of a sequence listing, figure, table, electronic medium, or the like.

The phrases "DNA sequence," "nucleic acid sequence," and "nucleic acid molecule" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

The term "expression" refers to the transcription of a gene to produce the corresponding mRNA and translation of this mRNA to produce the corresponding gene product (i.e., a peptide, polypeptide, or protein).

The phrase "expression of antisense RNA" refers to the transcription of a DNA to produce a first RNA molecule capable of hybridizing to a second RNA molecule.

The term "homology" refers to the level of similarity between two or more nucleic acid or amino acid sequences in terms of percent of positional identity (i.e., sequence similarity or identity). Homology also refers to the concept of similar functional properties among different nucleic acids or proteins.

The term "heterologous" refers to the relationship between two or more nucleic acid or protein sequences that are derived from different sources. For example, a promoter is heterologous with respect to a coding sequence if such a combination is not normally found in nature. In addition, a particular sequence may be "heterologous" with respect to a cell or organism into which it is inserted (i.e., does not naturally occur in that particular cell or organism).

The term "hybridization" refers to the ability of a first strand of nucleic acid to join with a second strand via hydrogen bond base pairing when the two nucleic acid strands have sufficient sequence identity. Hybridization occurs when the two nucleic acid molecules anneal to one another under appropriate conditions.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence.

The term or phrase "promoter" or "promoter region" refers to a nucleic acid sequence, usually found upstream (5') to a coding sequence, that is capable of directing transcription of a nucleic acid sequence into mRNA. The promoter or promoter region typically provides a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

The phrase "5' UTR" refers to the transcribed, but untranslated region of DNA upstream, or 5', of the coding region of a gene. A promoter is often used in combination with its native 5' UTR in practice. In other cases, a promoter is used in combination with a heterologous 5' UTR to achieve optimal expression.

The phrase "3'UTR" refers to the untranslated region of DNA downstream, or 3', of the coding region of a gene. The 3' UTR contains signals for transcription termination and RNA polyadenylation.

The phrase "recombinant vector" refers to any agent such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source and is capable of genomic integration or autonomous replication.

The phrase "Regulatory sequence" refers to a nucleotide sequence located upstream (5'), within, or downstream (3') to a coding sequence. Transcription and expression of the coding sequence is typically impacted by the presence or absence of the regulatory sequence.

The phrase "substantially homologous" refers to two sequences which are at least about 90% identical in sequence, as measured by the BestFit program described herein (Version 10; Genetics Computer Group, Inc., University of Wisconsin Biotechnology Center, Madison, Wis.), using default parameters.

The term "transformation" refers to the introduction of nucleic acid into a recipient host. The term "host" refers to bacteria cells, fungi, animals or animal cells, plants or seeds, or any plant parts or tissues including plant cells, protoplasts, calli, roots, tubers, seeds, stems, leaves, seedlings, embryos, and pollen.

As used herein, the phrase "transgenic plant" refers to a plant having an introduced nucleic acid stably integrated into a genome of the plant, for example, the nuclear or plastid genomes.

As used herein, the phrase "substantially purified" refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

In a preferred aspect, a similar genetic background is a background where the organisms being compared share 50% or greater of their nuclear genetic material. In a more preferred aspect a similar genetic background is a background where the organisms being compared share 75% or greater, even more preferably 90% or greater of their nuclear genetic material. In another even more preferable aspect, a similar genetic background is a background where the organisms being compared are plants, and the plants are isogenic except for any genetic material originally introduced using plant transformation techniques.

DETAILED DESCRIPTION OF THE PREFERRED EMBODIMENTS

The present invention provides promoters capable of transcribing a heterologous structural nucleic acid sequence in a seed, and methods of modifying, producing, and using the same. The invention also provides compositions, transformed host cells and plants containing seed specific promoters, and methods for preparing and using the same.

Nucleic Acid Molecules

The present invention provides nucleic acid molecules comprising a sequence selected from the group consisting of SEQ ID NOs: 1-4 and complements thereof. SEQ ID NO: 1 represents a sle2 gene promoter. SEQ ID NO: 2 represents a lea9 promoter. SEQ ID NO: 3 represents an AtPer1 promoter. SEQ ID NO: 4 represents a lectin promoter.

Nucleic acid hybridization is a technique well known to those of skill in the art of DNA manipulation. The hybridization property of a given pair of nucleic acids is an indication of their similarity or identity.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C.

High stringency conditions may be used to select for nucleic acid sequences with higher degrees of identity to the disclosed nucleic acid sequences (Sambrook et al., 1989).

The high stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5× Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. The high stringency conditions are preferably provided by 6×SSC, 5× Denhardt's solution, 100 mg/mL fish sperm DNA, and 0.1% (w/v) SDS, with an incubation at 55° C. for several hours.

The hybridization is generally followed by several wash steps. The wash compositions generally comprise 0.5× to about 10×SSC, and 0.01% (w/v) to about 0.5% (w/v) SDS with a 15 minute incubation at about 20° C. to about 70° C.

Preferably, the nucleic acid segments remain hybridized after washing at least one time in 0.1×SSC at 65° C.

The nucleic acid molecules of the present invention preferably hybridize, under high stringency conditions, with a nucleic acid molecule having the sequence selected from the group consisting of SEQ ID NOs: 1-4 and complements thereof. In a preferred embodiment, a nucleic acid molecule of the present invention hybridizes, under high stringency conditions, with a nucleic acid molecule comprising SEQ ID NO: 1. In a preferred embodiment, a nucleic acid molecule of the present invention hybridizes, under high stringency conditions, with a nucleic acid molecule comprising SEQ ID NO: 2. In a preferred embodiment, a nucleic acid molecule of the present invention hybridizes, under high stringency conditions, with a nucleic acid molecule comprising SEQ ID NO: 3. In a preferred embodiment, a nucleic acid molecule of the present invention hybridizes, under high stringency conditions, with a nucleic acid molecule comprising SEQ ID NO: 4.

In a preferred embodiment, a nucleic acid molecule of the present invention comprises a nucleic acid sequence that has a sequence identity to SEQ ID NOs: 1, 2, 3, or 4 of greater than about 75, about 80, about 85, about 90, about 91, about 92, about 93, about 94, about 95, about 96, about 97, about 98, or about 99%.

The percent of sequence identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, 1981; Smith et al., 1983). The percent identity is most preferably determined using the "Best Fit" program using default parameters.

The present invention also provides nucleic acid molecule fragments that exhibit a percent identity to any of SEQ ID NO: 1-4 and complements thereof. In an embodiment, the fragments are between 50 and 600 consecutive nucleotides, 50 and 550 consecutive nucleotides, 50 and 500 consecutive nucleotides, 50 and 450 consecutive nucleotides, 50 and 400 consecutive nucleotides, 50 and 350 consecutive nucleotides, 50 and 300 consecutive nucleotides, 50 and 250 consecutive nucleotides, 50 and 200 consecutive nucleotides, 50 and 150 consecutive nucleotides, 50 and 100, 15 to 100, 15 to 50, or 15 to 25 consecutive nucleotides of a nucleic molecule of the present invention.

In another embodiment, the fragment comprises at least about 15, 20, 30, 40, 50, 60, 70, 80, 90, 100, 150, 200, 250, 300, 350, 400, 450, 500, 550, 600, or about 650 consecutive nucleotides of a nucleic acid sequence of the present invention.

The present invention contemplates nucleic acid sequences encoding polypeptides having the enzyme activity of the steroid pathway enzymes squalene epoxidase, sterol methyl transferase I, sterol C4 demethylase, obtusifoliol C14α-demethylase, sterol C5 desaturase and sterol methyl transferase II.

Squalene epoxidase (also called squalene monooxygenase) catalyzes the conversion of squalene to squalene epoxide (2,3-oxidosqualene), a precursor to the initial sterol molecule in phytosterol biosynthetic pathway, cycloartenol. This is the first reported step in the pathway where oxygen is required for activity. The formation of squalene epoxide is also the last common reported step in sterol biosynthesis of animals, fungi and plants. Recently, several homologues of *Arabidopsis* and *Brassica* squalene epoxidase genes are reported (Schafer, U. A.; Reed, D. W.; Hunter, D. G.; Yao, K.; Weninger, A. M.; Tsang, E. W.; Reaney, M. J.; MacKenzie, S. L.; and Covello, P. S,. (1999) *Plant Mol. Biol.,* 39(4):721-728). The same authors also have PCT application disclosing the use of antisense technology with squalene epoxidase to elevate squalene levels in plants (WO 97/34003).

Squalene Epoxidase, also known as squalene monooxygenase is enzyme reference number 1.14.99.7, *Enzyme Nomenclature,* 1992, p. 146.

Several squalene epoxidase enzymes are known to the art. These include *Arabidopsis* squalene epoxidase protein sequence Accession No. AC004786, *Arabidopsis* squalene epoxidase Accession No. N64916, and *Arabidopsis* squalene epoxidase Accession No. T44667. Japanese Patent Application 07 194 381 A discloses a DNA encoding a mammalian squalene epoxidase.

An additional aspect of the invention is the recombinant constructs and vectors comprising nucleic acid sequences encoding squalene epoxidase, as well as a method of producing the novel squalene epoxidase, comprising culturing a host cell transformed with the novel constructs or vectors for a time and under conditions conductive to the production of the squalene epoxidase, and recovering the squalene epoxidase produced thereby.

S-adenosyl-L-methionine:sterol C24 methyl transferases (SMT1 and SMT2) catalyze the transfer of a methyl group from a cofactor, S-adenosyl-L-methionine, to the C24 center of the sterol side chain (Bach, T. J. and Benveniste, P. (1997), *Prog. Lipid Res.,* 36:197-226). SMT in higher plant cells are responsible for their capability to produce a mixture of 24-methyl and 24-ethyl sterols (Schaffer, A.; Bouvier-Navé, Benveniste, P.; Schaller, H.; (2000) *Lipids,* 35:263-269). Functional characterization of the SMT using a yeast erg6 expression system demonstrated unambiguously that an SMT1 sequence encodes a cycloartenol-C24-methyltransferase and a SMT2 sequence encodes a 24-methylene lophenol-C24-methyltransferase in a given plant species (Bouvier-Navé, P.; Husselstein, T.; and Benveniste, P. (1998), *Eur. J. Biochem.,* 246:518-529). Several plant genes coding for SMT1 and SMT2 have been reported and reviewed (Schaffer, A.; Bouvier-Navé, Benveniste, P.; Schaller, H. (2000) *Lipids,* 35:263-269). Transgenic plants expressing homologues of either SMT1 or SMT2 have been studied (Schaffer, A.; Bouvier-Navé, Benveniste, P.; Schaller, H. (2000) *Lipids,* 35:263-269). The use of these genes to modify plant sterol composition are also covered by two patent applications (WO 98/45457 and WO 00/61771).

Sterol methyl transferase I enzymes known in the art are useful in the present invention. Exemplary sequences include the known *Arabidopsis* sterol methyl transferase I protein sequence Accession No. U71400, the known tobacco sterol methyl transferase I protein sequence Accession No. U81312 and *Ricinus communis* sterol C methyltransferase, *Eur. J. Biochem.,* 246(2);518-529 (1997). (Complete cds, Accession No. g2246457).

S-Adenosyl-L-Methionine Sterol C24 Methyltransferase—A nucleic acid sequence encoding an *Arabidopsis thaliana* S-adenosyl-L-methionine-sterol C24 methyltransferase has been published by Husselstein et al. (1996) *FEBS Letters* 381:87-92. $\Delta^{24}$-sterol C-methyltransferase is enzyme number 2.1.1.41, *Enzyme Nomenclature* 1992, page 160.

Sterol C4 demethylase catalyses the first of several demethylation reactions, which results in the removal of the two methyl groups at C4. While in animals and fungi the removal of the two C4 methyl groups occurs consecutively, in plants it has been reported that there are other steps between the first and second C4 demethylations (Bach, T. J. and Benveniste, P. (1997), *Prog. Lipid Res.*, 36:197-226). The C4 demethylation is catalyzed by a complex of microsomal enzymes consisting of a monooxygenase, an NAD$^+$-dependent sterol C4 decarboxylase, and an NADPH-dependent 3-ketosteroid reductase.

Sterol C14 demethylase catalyzes demethylation at C14 which removes the methyl group at C14 and creates a double bond at that position. In both fungi and animals, this is the first step in the sterol synthesis pathway. However, in higher plants, the 14α-methyl is removed after one C4 methyl has disappeared. Thus, while lanosterol is the substrate for C14 demethylase in animal and fungal cells, the plants enzyme uses obtusifoliol as substrate. Sterol C14 demethylation is mediated by a cytochrome P-450 complex. The mechanism of 14-methyl removal involves two oxidation steps leading to an alcohol, then an aldehyde at C29 and a further oxidative step involving a deformylation leading to formic acid and the sterol product with a typical 8,14-diene (Aoyama, Y.; Yoshida, Y.; Sonoda, Y.; and Sato, Y. (1989) *J. Biol. Chem.*, 264:18502-18505). Obtusifoliol C14α-demethylase from *Sorghum bicolor* (L) Moench has been cloned using a gene-specific probe generated using PCR primers designed from an internal 14 amino acid sequence and was functionally expressed in *E. coli* (Bak, S.; Kahn, R. A.; Olsen, C. E.; and Halkier, B. A. (1997) *The Plant Journal*, 11(2):191-201). Also, *Saccharomyces cerevisiae* CYP51A1 encoding lanosterol C14 demethylase was functionally expressed in tobacco (Grausem, B.; Chaubet, N.; Gigot, C.; Loper, J. C.; and Benveniste, P. (1995) *The Plant Journal*, 7(5):761-770).

Sterol C14 demethylase enzymes and sequences are known in the art. For example *Sorghum bicolor* obtusifoliol C14α-demethylase CYP51 mRNA, described in *Plant J.*, 11(2):191-201 (1997) (complete cds Acession No. U74319).

An additional aspect of the invention is the recombinant constructs and vectors comprising nucleic acid sequences encoding obtusifoliol C14α-demethylase, as well as a method of producing obtusifoliol C14α-demethylase, comprising culturing a host cell transformed with the novel constructs or vectors for a time and under conditions conductive to the production of the obtusifoliol C14α-demethylase, and recovering the obtusifoliol C14 α-demethylase produced thereby.

Sterol C5 desaturase catalyzes the insertion of the $\Delta^5$-double bond that normally occurs at the $\Delta^7$-sterol level, thereby forming a $\Delta^{5,7}$-sterol (Parks et al., *Lipids*, 30:227-230 (1995)). The reaction has been reported to involve the stereospecific removal of the 5α and 6α hydrogen atoms, biosynthetically derived from the 4 pro-R and 5 pro-S hydrogens of the (+) and (−) R-mevalonic acid, respectively (Goodwin, T. W. (1979) *Annu. Rev. Plant Physiol.*, 30:369-404). The reaction is obligatorily aerobic and requires NADPH or NADH. The desaturase has been reported to be a multienzyme complex present in microsomes. It consists of the desaturase itself, cytochrome $b_5$ and a pyridine nucleotide-dependent flavoprotein. The $\Delta^5$-desaturase is reported to be a mono-oxygenase that utilizes electrons derived from a reduced pyridine nucleotide via cytochrome$_b$ (Taton, M., and Rahier, A. (1996) *Arch. Biochem. Biophys.*, 325:279-288). An *Arabidopsis thaliana* cDNA encoding a sterol C5 desaturase was cloned by functional complementation of a yeast mutant, erg3 defective in ERG3, the gene encoding the sterol C5 desaturase required for ergosterol biosynthesis (Gachotte D.; Husselstein, T.; Bard, M.; Lacroute F.; and Benveniste, P. (1996) *The Plant Journal*, 9(3):391-398). Known sterol C5 desaturase enzymes are useful in the present invention, including *Arabidopsis* sterol C5 desaturase protein sequence Accession No. X90454, and the *Arabidopsis thaliana* mRNA for sterol C5 desaturase described in *Plant J.* 9(3):391-398 (1996) (complete cds Accession No. g1061037).

The NCBI (National Center for Biotechnology Information) database shows 37 sequences for sterol desaturase that are useful in the present invention. The following are exemplary of such sequences. From yeast: C5 sterol desaturase NP_013157 (*Saccharomyces cerevisiae*); hypothetical C5 sterol desaturase-fission T40027 (*Schizosaccharomyces pombe*); C5 sterol desaturase-fission T37759 (*Schizosaccharomyces pombe*); C5 sterol desaturase JQ1146 (*Saccharomyces cerevisiae*); C5 sterol desaturase BAA21457 (*Schizosaccharomyces pombe*); C5 sterol desaturase CAA22610 (*Schizosaccharomyces pombe*); putative C5 sterol desaturase CAA16898 (*Schizosaccharomyces pombe*); probable C5 sterol desaturase O13666 (erg3_schpo); C5 sterol desaturase P50860 (Erg3_canga); C5 sterol desaturase P32353 (erg3_yeast); C5,6 desaturase AAC99343 (*Candida albicans*); C5 sterol desaturase BAA20292 (*Saccharomyces cerevisiae*); C5 sterol desaturase AAB39844 (*Saccharomyces cerevisiae*); C5 sterol desaturase AAB29844 (*Saccharomyces cerevisiae*); C5 sterol desaturase CAA64303 (*Saccharomyces cerevisiae*); C5 sterol desaturase AAA34595 (*Saccharomyces cerevisiae*); C5 sterol desaturase AAA34594 (*Saccharomyces cerevisiae*). From plants: C5 sterol desaturase S71251 (*Arabidopsis thaliana*); putative sterol C5 desaturase AAF32466 (*Arabidopsis thaliana*); sterol C5 desaturase AAF32465 (*Arabidopsis thaliana*); putatuve sterol desaturase AAF22921 (*Arabidopsis thaliana*); $\Delta^7$-sterol C5 desaturase (*Arabidopsis thaliana*); sterol C5(6) desaturase homolog AAD20458 (*Nicotiana tabacum*); sterol C5 desaturase AAD12944 (*Arabidopsis thaliana*); sterol C5,6 desaturase AAD04034 (*Nicotiana tabacum*); sterol C5 desaturase CAA62079 (*Arabidopsis thaliana*). From mammals: sterol C5 desaturase (*Mus musculus*) BAA33730; sterol C5 desaturase BAA33729 (*Homo sapiens*); lathosterol oxidase CAB65928 (*Leishmania major*); lathosterol oxidase (lathosterol 5 desaturase) O88822 (*Mus musculus*); lathosterol 5 desaturase O75845 (*Homo sapiens*); $\Delta^7$-sterol C5 desaturase AAF00544 (*Homo sapiens*). Others: fungal sterol C5 desaturase homolog BAA18970 (*Homo sapiens*).

For DNA sequences encoding a sterol C5 desaturase useful in the present invention, the NCBI_nucleotide search for "sterol desaturase" came up with 110 sequences. The following are exemplary of such sequences. NC_001139 (*Saccharomyces cerevisiae*); NC 001145 (*Saccharomyces cerevisiae*); NC_001144 (*Saccharomyces cerevisiae*); AW700015 (*Physcomitrella patens*); AB004539 (*Schizosaccharomyces pombe*); and AW596303 (*Glycine max*); AC012188 (*Arabidopsis thaliana*).

The combination of introduction of an HMG-CoA reductase gene along with a sterol methyl transferase II gene into a cell serves to reduce steroid pathway intermediate compound accumulation in addition to reducing the accumulation of 24-methyl sterols such as campesterol.

Known sterol methyl transferase II enzymes are useful in the present invention, including *Arabidopsis* sterol methyl transferase II protein sequence (complete mRNA cds from *FEBS Lett.*, 381(12):87-92 (1996) Accession No. X89867).

Recombinant constructs encoding any of the forgoing enzymes affecting the steroid biosynthetic pathway can be incorporated into recombinant vectors comprising the bacterial or plant expression vectors.

In a preferred embodiment, any of the plants or organisms of the present invention are transformed with a nucleic acid of the present invention and a gene encoding a member selected from the group consisting of squalene epoxidase, sterol methyl transferase I, sterol C4 demethylase, obtusifoliol C14α-demethylase, sterol C5 desaturase, and sterol methyl transferase II. In a preferred embodiment, a plant or organism of the present invention is transformed with one or more of SEQ ID NOs: 1-4 and a gene encoding a member selected from the group consisting of squalene epoxidase, sterol methyl transferase I, sterol C4 demethylase, obtusifoliol C14α-demethylase, sterol C5 desaturase, and sterol methyl transferase II. In a further preferred embodiment, a plant or organism of the present invention is transformed with one or more of SEQ ID NOs: 1-4, a gene encoding a member selected from the group consisting of squalene epoxidase, sterol methyl transferase I, sterol C4 demethylase, obtusifoliol C14α-demethylase, sterol C5 desaturase, and sterol methyl transferase II, and one or more genes encoding a tocopherol pathway enzyme as disclosed elsewhere herein. In a further preferred embodiment, a plant or organism of the present invention is transformed with one or more of SEQ ID NOs: 1-4, two genes encoding a member selected from the group consisting of squalene epoxidase, sterol methyl transferase I, sterol C4 demethylase, obtusifoliol C14α-demethylase, sterol C5 desaturase, and sterol methyl transferase II, and two genes encoding a tocopherol pathway enzyme as disclosed elsewhere herein. Any of the above combinations of tocopherol and sterol biosynthesis genes can be introduced into a plant on one or more constructs or vectors, as is known in the art and described herein.

Promoters

In one embodiment any of the disclosed nucleic acid molecules may be promoters. In a preferred embodiment, the promoter is tissue or organ specific, and preferably seed specific. In a particularly preferred embodiment the promoter preferentially expresses associated structural genes in the endosperm or embryo. In a preferred embodiment, the promoter preferentially drives expression of the associated structural genes during a defined period of embryogenesis in seed.

In one aspect, a promoter is considered tissue or organ specific if the level of an mRNA in that tissue or organ is expressed at a level that is at least 10 fold higher, preferably at least 100 fold higher or at least 1,000 fold higher than another tissue or organ. The level of mRNA can be measured either at a single time point or at multiple time points and as such the fold increase can be average fold increase or an extrapolated value derived from experimentally measured values. As it is a comparison of levels, any method that measures mRNA levels can be used. In a preferred aspect, the tissue or organs compared are a seed or seed tissue with a leaf or leaf tissue. In another preferred aspect, multiple tissues or organs are compared. A preferred multiple comparison is a seed or seed tissue compared with two, three, four or more tissues or organs selected from the group consisting of floral tissue, floral apex, pollen, leaf, embryo, shoot, leaf primordia, shoot apex, root, root tip, vascular tissue and cotyledon. As used herein, examples of plant organs are seed, leaf, root, etc. and example of tissues are leaf primordia, shoot apex, vascular tissue etc. The activity or strength of a promoter may be measured in terms of the amount of mRNA or protein accumulation it specifically produces, relative to the total amount of mRNA or protein at a single time point or at multiple time points in the specific tissue during the growth and development. The temporal profile of a promoter may be obtained by compare the relative strength of the promoter in the tissues collected at multiple time points during the growth and development.

Alternatively, the temporal profile of a promoter may be expressed relative to a well-characterized promoter (for which expression profile was previously assessed). For example, a promoter of interest may be operably linked to a reporter sequence (e.g., GUS) and introduced into a specific cell type. A known promoter may be similarly prepared and introduced into the same cellular context. Transcriptional activity of the promoter of interest is then determined by comparing the timing of reporter expression, relative to that of the known promoter. The cellular context is preferably soybean.

Structural Nucleic Acid Sequences

The promoters of the present invention may be operably linked to a structural nucleic acid sequence that is heterologous with respect to the promoter. The structural nucleic acid sequence may generally be any nucleic acid sequence for which an increased level of transcription is desired. The structural nucleic acid sequence preferably encodes a polypeptide that is suitable for incorporation into the diet of a human or an animal or provides some other agriculturally important feature.

Suitable structural nucleic acid sequences include, without limitation, those encoding seed storage proteins, fatty acid pathway enzymes, tocopherol biosynthetic enzymes, amino acid biosynthetic enzymes, steroid pathway enzymes, and starch branching enzymes.

Preferred seed storage proteins include zeins (U.S. Pat. Nos. 4,886,878; 4,885,357; 5,215,912; 5,589,616; 5,508,468; 5,939,599; 5,633,436; and 5,990,384; Patent Applications WO 90/01869, WO 91/13993, WO 92/14822, WO 93/08682, WO 94/20628, WO 97/28247, WO 98/26064, and WO 99/40209), 7S proteins (U.S. Pat. Nos. 5,003,045 and 5,576, 203), Brazil nut protein (U.S. Pat. No. 5,850,024), phenylalanine free proteins (Patent Application WO 96/17064), albumin (Patent Application WO 97/35023), β-conglycinin (Patent Application WO 00/19839), 11S (U.S. Pat. No. 6,107, 051), α-hordothionin (U.S. Pat. Nos. 5,885,802 and 5,885, 801), arcelin seed storage proteins (U.S. Pat. No. 5,270,200), lectins (U.S. Pat. No. 6,110,891), and glutenin (U.S. Pat. Nos. 5,990,389 and 5,914,450).

Preferred fatty acid pathway enzymes include thioesterases (U.S. Pat. Nos. 5,512,482; 5,530,186; 5,945, 585; 5,639,790; 5,807,893; 5,955,650; 5,955,329; 5,759,829; 5,147,792; 5,304,481; 5,298,421; 5,344,771; and 5,760,206), and desaturases (U.S. Pat. Nos. 5,689,050; 5,663,068; 5,614, 393; 5,856,157; 6,117,677; 6,043,411; 6,194,167; 5,705,391; 5,663,068; 5,552,306; 6,075,183; 6,051,754; 5,689,050; 5,789,220; 5,057,419; 5,654,402; 5,659,645; 6,100,091; 5,760,206; 6,172,106; 5,952,544; 5,866,789; 5,443,974; and 5,093,249). Preferred tocopherol biosynthetic enzymes include tyrA, slr1736, ATPT2, dxs, dxr, GGPPS, HPPD, GMT, MT1, tMT2, AANT1, slr1737, and an antisense construct for homogentisic acid dioxygenase (Kridl et al., *Seed Sci. Res.*, 1:209:219 (1991); Keegstra, *Cell*, 56(2):247-53 (1989); Nawrath, et al., *Proc. Natl. Acad. Sci. (U.S.A.)*, 91:12760-12764 (1994); xia et al., *J. Gen. Microbiol.*, 138: 1309-1316 (1992); Cyanobase http://www.kazusa.or.jp/cyanobase; Lois et al., *Proc. Natl. Acad. Sci. (U.S.A.)*, 95(5): 2105-2110 (1998); Takahashi et al. *Proc. Natl. Acad. Sci. (U.S.A.)*, 95(17):9879-9884 (1998); Norris et al., *Plant Physiol.*, 117:1317-1323 (1998); Bartley and Scolnik, *Plant Physiol.*, 104:1469-1470 (1994); Smith et al., *Plant J.*, 11:83-92 (1997); WO 00/32757; WO 00/10380; Saint Guily, et al., *Plant Physiol.*, 100(2):1069-1071 (1992); Sato et al., *J. DNA Res.*, 7(1):31-63 (2000)).

Various genes and their encoded proteins that are involved in tocopherol biosynthesis are listed in the table below.

| Gene ID | Enzyme name |
| --- | --- |
| tyrA | Prephanate dehydrogenase |
| slr1736 | Phytylprenyl transferase from Synechocystis |
| ATPT2 | Phytylprenyl transferase from *Arabidopsis thaliana* |
| DXS | 1-Deoxyxylulose-5-phosphate synthase |
| DXR | 1-Deoxyxylulose-5-phosphate reductoisomerase |
| GGPPS | Geranylgeranyl pyrophosphate synthase |
| HPPD | p-Hydroxyphenylpyruvate dioxygenase |
| AANT1 | Adenylate transporter |
| slr1737 | Tocopherol cyclase |
| IDI | Isopentenyl diphosphate isomerase |
| GGH | Geranylgeranyl reductase |
| GMT | Gamma Methyl Transferase |

The "Gene IDs" given in the table above identify the gene associated with the listed enzyme. Any of the Gene IDs listed in the table appearing herein in the present disclosure refer to the gene encoding the enzyme with which the Gene ID is associated in the table. Preferred amino acid biosynthetic enzymes include anthranilate synthase (U.S. Pat. No. 5,965,727; Patent Applications WO 97/26366, WO 99/11800, and WO 99/49058), tryptophan decarboxylase (Patent Application WO 99/06581), threonine decarboxylase (U.S. Pat. Nos. 5,534,421 and 5,942,660; Patent Application WO 95/19442), threonine deaminase (Patent Applications WO 99/02656, and WO 98/55601), and aspartate kinase (U.S. Pat. Nos. 5,367,110; 5,858,749; and 6,040,160).

Preferred starch branching enzymes include those set forth in U.S. Pat. Nos. 6,232,122 and 6,147,279; and Patent Application WO 97/22703.

Alternatively, a promoter and structural nucleic acid sequence may be designed to down-regulate a specific nucleic acid sequence. This is typically accomplished by linking the promoter to a structural nucleic acid sequence that is oriented in the antisense direction. One of ordinary skill in the art is familiar with such antisense technology. Any nucleic acid sequence may be negatively regulated in this manner.

Targets of such regulation may include polypeptides that have a low content of essential amino acids, yet are expressed at a relatively high level in a particular tissue. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived feed or to down-regulate catabolic enzymes involved in degradation of desired compounds such as essential amino acids.

Modified Structural Nucleic Acid Sequences

The promoters of the present invention may also be operably linked to a modified structural nucleic acid sequence that is heterologous with respect to the promoter. The structural nucleic acid sequence may be modified to provide various desirable features. For example, a structural nucleic acid sequence may be modified to increase the content of essential amino acids, enhance translation of the amino acid sequence, alter post-translational modifications (e.g., phosphorylation sites), transport a translated product to a compartment inside or outside of the cell, improve protein stability, insert or delete cell signaling motifs, increase plant cell or organ size, and the like.

In a preferred embodiment, the structural nucleic acid sequence is enhanced to encode a polypeptide having an increased content of at least one, and more preferably 2, 3, or 4 of the essential amino acids selected from the group consisting of histidine, lysine, methionine, and phenylalanine. Non-essential amino acids may also be added, as needed, for structural and nutritive enhancement of the polypeptide. Structural nucleic acid sequences particularly suited to such enhancements include those encoding native polypeptides that are expressed at relatively high levels, have a particularly low content of essential amino acids, or both. Examples of such are the seed storage proteins, such as glycinin and β-conglycinin. Other suitable targets include arcelin, phaseolin, lectin, zeins, and albumin.

Codon Usage in Structural Nucleic Acid Sequences

Due to the degeneracy of the genetic code, different nucleotide codons may be used to code for a particular amino acid. A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any of the above described nucleic acid and amino acid sequences may be modified to reflect the preferred codon usage of a host cell or organism in which they are contained. Modification of a structural nucleic acid sequence for optimal codon usage in plants is described in U.S. Pat. No. 5,689,052.

Other Modifications of Structural Nucleic Acid Sequences

Additional variations in the structural nucleic acid sequences described above may encode proteins having equivalent or superior characteristics when compared to the proteins from which they are engineered. Mutations may include deletions, insertions, truncations, substitutions, fusions, shuffling of motif sequences, and the like.

Mutations to a structural nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a structural nucleic acid sequence. Examples include single strand rescue (Kunkel et al., 1985), unique site elimination (Deng and Nickloff, 1992), nick protection (Vandeyar et al., 1988), and PCR (Costa et al., 1996). Random or non-specific mutations may be generated by chemical agents (for a general review, see Singer and Kusmierek, 1982) such as nitrosoguanidine (Cerda-Olmedo et al., 1968; Guerola et al., 1971) and 2-aminopurine (Rogan and Bessman, 1970); or by biological methods such as passage through mutator strains (Greener et al., 1997). Additional methods of making the alterations described above are described by Ausubel et al. (1995); Bauer et al. (1985); Craik (1985); Frits Eckstein et al. (1982); Sambrook et al. (1989); Smith et al. (1981); and Osuna et al. (1994).

The modifications may result in either conservative or non-conservative changes in the amino acid sequence. Conservative changes are changes which do not alter the final amino acid sequence of the protein. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between about 1 and about 5 conservative changes.

Non-conservative changes include additions, deletions, and substitutions which result in an altered amino acid sequence. In a preferred embodiment, the protein has between about 5 and about 500 non-conservative amino acid changes, more preferably between about 10 and about 300 non-conservative amino acid changes, even more preferably between about 25 and about 150 non-conservative amino acid changes, and most preferably between about 5 and about 25 non-conservative amino acid changes or between about 1 and about 5 non-conservative changes.

Modifications may be made to the protein sequences described herein and the nucleic acid sequences which encode them that maintain the desired properties of the molecule. The following is a discussion based upon changing the amino acid sequence of a protein to create an equivalent, or possibly an improved, second-generation molecule. The amino acid changes may be achieved by changing the codons of the structural nucleic acid sequence, according to the codons given in the table below.

Codon degeneracy of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

Certain amino acids may be substituted for other amino acids in a protein sequence without appreciable loss of the desired activity. It is thus contemplated that various changes may be made in peptide sequences or protein sequences, or their corresponding nucleic acid sequences without appreciable loss of the biological activity.

In making such changes, the hydropathic index of amino acids may be considered. The importance of the hydropathic amino acid index in conferring interactive biological function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics. These are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, (i.e., still obtain a biologically functional protein). In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, (i.e., still obtain a biologically functional protein). In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted proteins have improved rumen resistance, increased resistance to proteolytic degradation, or both improved rumen resistance and increased resistance to proteolytic degradation, relative to the unmodified polypeptide from which they are engineered. Alternatively, changes could be made to improve kinetics of metabolic enzymes.

In a preferred aspect, the protein modified is selected from seed storage proteins, fatty acid pathway enzymes, tocopherol biosynthetic enzymes, amino acid biosynthetic enzymes and starch branching enzymes.

Recombinant Vectors

Any of the promoters and structural nucleic acid sequences described above may be provided in a recombinant vector. A recombinant vector typically comprises, in a 5' to 3' orientation: a promoter to direct the transcription of a structural nucleic acid sequence and a structural nucleic acid sequence. Suitable promoters and structural nucleic acid sequences include those described herein. The recombinant vector may further comprise a 3' transcriptional terminator, a 3' polyadenylation signal, other untranslated nucleic acid sequences, transit and targeting nucleic acid sequences, selectable markers, enhancers, and operators, as desired.

Means for preparing recombinant vectors are well known in the art. Methods for making recombinant vectors particularly suited to plant transformation are described in U.S. Pat. Nos. 4,971,908; 4,940,835; 4,769,061; and 4,757,011. These types of vectors have also been reviewed (Rodriguez et al., 1988; Glick et al., 1993).

Typical vectors useful for expression of nucleic acids in higher plants are well known in the art and include vectors derived from the tumor-inducing (Ti) plasmid of *Agrobacterium tumefaciens* (Rogers et al., 1987). Other recombinant vectors useful for plant transformation, including the pCaMVCN transfer control vector, have also been described (Fromm et al., 1985).

In one embodiment, multiple promoters are operably linked in a single construct to any combination of structural genes. In a preferred embodiment, any combination of 1, 2, 3, 4, 5, or 6 or more of nucleic acid molecules comprising SEQ ID NOs: 1-4 can be operatively linked in a single construct to any combination of structural genes. In another aspect of the preferred embodiment, the nucleic acid molecules may be modified. Such modifications can include, for example, removal or addition of one or more structural or functional elements.

Additional Promoters in the Recombinant Vector

One or more additional promoters may also be provided in the recombinant vector. These promoters may be operably linked, for example, without limitation, to any of the structural nucleic acid sequences described above. Alternatively, the promoters may be operably linked to other nucleic acid sequences, such as those encoding transit peptides, selectable marker proteins, or antisense sequences.

These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity. In plants, promoters that are inducible, of viral or synthetic origin, constitutively active, temporally regulated, and spatially regulated have been described (Poszkowski et al., 1989; Odell et al., 1985; Chau et al., 1989).

Often-used constitutive promoters include the CaMV 35S promoter (Odell et al., 1985), the enhanced CaMV $^{35}$S promoter, the Figwort Mosaic Virus (FMV) promoter (Richins et al., 1987), the mannopine synthase (mas) promoter, the nopaline synthase (nos) promoter, and the octopine synthase (ocs) promoter.

Useful inducible promoters include promoters induced by salicylic acid or polyacrylic acids (PR-1; Williams et al., 1992), induced by application of safeners (substituted benzenesulfonamide herbicides; Hershey and Stoner, 1991), heat-shock promoters (Ou-Lee et al., 1986; Ainley et al., 1990), a nitrate-inducible promoter derived from the spinach nitrite reductase structural nucleic acid sequence (Back et al., 1991), hormone-inducible promoters (Yamaguchi-Shinozaki et al., 1990; Kares et al., 1990), and light-inducible promoters associated with the small subunit of RuBP carboxylase and LHCP families (Kuhlemeier et al., 1989; Feinbaum et al., 1991; Weisshaar et al., 1991; Lam and Chua, 1990; Castresana et al., 1988; Schulze-Lefert et al., 1989).

Examples of useful tissue or organ specific promoters include β-conglycinin, (Doyle et al., 1986; Slighton and Beachy, 1987), and other seed specific promoters (Knutzon et al., 1992; Bustos et al., 1991; Lam and Chua, 1991). Plant functional promoters useful for preferential expression in seed include those from plant storage proteins and from proteins involved in fatty acid biosynthesis in oilseeds. Examples of such promoters include the 5' regulatory regions from such structural nucleic acid sequences as napin (Kridl et al., 1991), phaseolin, zein, soybean trypsin inhibitor, ACP, stearoyl-ACP desaturase, and oleosin. Seed-specific regulation is further discussed in European Patent 0 255 378.

Another exemplary seed specific promoter is a lectin promoter. The lectin protein in soybean seeds is encoded by a single structural nucleic acid sequence (Lel) that is only expressed during seed development. A lectin structural nucleic acid sequence and seed-specific promoter have been characterized and used to direct seed specific expression in transgenic tobacco plants (Vodkin et al., 1983; Lindstrom et al., 1990).

Particularly preferred additional promoters in the recombinant vector include the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco (Mandel et al., 1995); corn sucrose synthetase 1 (Yang and Russell, 1990); corn alcohol dehydrogenase 1 (Vogel et al., 1989); corn light harvesting complex (Simpson, 1986); corn heat shock protein (Odell et al., 1985); the chitinase promoter from *Arabidopsis* (Samac et al., 1991); the LTP (Lipid Transfer Protein) promoters from broccoli (Pyee et al., 1995); petunia chalcone isomerase (Van Tunen et al., 1988); bean glycine rich protein 1 (Keller et al., 1989); potato patatin (Wenzler et al., 1989); the ubiquitin promoter from maize (Christensen et al., 1992); and the actin promoter from rice (McElroy et al., 1990).

An additional promoter is preferably seed selective, tissue selective, constitutive, or inducible. The promoter is most preferably the nopaline synthase (nos), octopine synthase (ocs), mannopine synthase (mas), cauliflower mosaic virus 19S and 35S (CaMV19S, CaMV35S), enhanced CaMV (eCaMV), ribulose 1,5-bisphosphate carboxylase (ss-RUBISCO), figwort mosaic virus (FMV), CaMV derived AS4, tobacco RB7, wheat POX1, tobacco EIF-4, lectin protein (Lel), or rice RC2 promoter.

Recombinant Vectors having Additional Structural Nucleic Acid Sequences

The recombinant vector may also contain one or more additional structural nucleic acid sequences. These additional structural nucleic acid sequences may generally be any sequences suitable for use in a recombinant vector. Such structural nucleic acid sequences include, without limitation, any of the structural nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e., a single operon).

The additional structural nucleic acid sequences include, without limitation, those encoding seed storage proteins, fatty acid pathway enzymes, tocopherol biosynthetic enzymes, amino acid biosynthetic enzymes, and starch branching enzymes.

Preferred seed storage proteins include zeins (U.S. Pat. Nos. 4,886,878; 4,885,357; 5,215,912; 5,589,616; 5,508,468; 5,939,599; 5,633,436; and 5,990,384; Patent Applications WO 90/01869, WO 91/13993, WO 92/14822, WO 93/08682, WO 94/20628, WO 97/28247, WO 98/26064, and WO 99/40209), 7S proteins (U.S. Pat. Nos. 5,003,045 and 5,576, 203), Brazil nut protein (U.S. Pat. No. 5,850,024), phenylalanine free proteins (Patent Application WO 96/17064), albumin (Patent Application WO 97/35023), β-conglycinin (Patent Application WO 00/19839), 11S (U.S. Pat. No. 6,107, 051), α-hordothionin (U.S. Pat. Nos. 5,885,802 and 5,88, 5801), arcelin seed storage proteins (U.S. Pat. No. 5,270, 200), lectins (U.S. Pat. No. 6,110,891), and glutenin (U.S. Pat. Nos. 5,990,389 and 5,914,450).

Preferred fatty acid pathway enzymes include thioesterases (U.S. Pat. Nos. 5,512,482; 5,530,186; 5,945, 585; 5,639,790; 5,807,893; 5,955,650; 5,955,329; 5,759,829; 5,147,792; 5,304,481; 5,298,421; 5,344,771; and 5,760,206), and desaturases (U.S. Pat. Nos. 5,689,050; 5,663,068; 5,614, 393; 5,856,157; 6,117,677; 6,043,411; 6,194,167; 5,705,391; 5,663,068; 5,552,306; 6,075,183; 6,051,754; 5,689,050; 5,789,220; 5,057,419; 5,654,402; 5,659,645; 6,100,091; 5,760,206; 6,172,106; 5,952,544; 5,866,789; 5,443,974; and 5,093,249).

Preferred tocopherol biosynthetic enzymes include tyrA, slr1736, ATPT2, dxs, dxr, GGPPS, HPPD, GMT, MT1, tMT2, AANT1, slr1737, and an antisense construct for homogentisic acid dioxygenase (Kridl et al., *Seed Sci. Res.*, 1:209-219 (1991); Keegstra, *Cell*, 56(2):247-53 (1989); Nawrath et al., *Proc. Natl. Acad. Sci. (U.S.A.)*, 91:12760-12764 (1994); Xia et al., *J. Gen. Microbiol.*, 138:1309-1316 (1992); Cyanobase http://www.kazusa.or.jp/cyanobase; Lois et al., *Proc. Natl. Acad. Sci. (U.S.A.)*, 95(5):2105-2110 (1998); Takahashi, et al. *Proc. Natl. Acad. Sci. (U.S.A.)*, 95(17):9879-9884 (1998); Norris et al., *Plant Physiol.*, 117: 1317-1323 (1998); Bartley and Scolnik, *Plant Physiol.*, 104: 1469-1470 (1994); Smith et al., *Plant J.*, 11:83-92 (1997); WO 00/32757; WO 00/10380; Saint Guily et al., *Plant Physiol.*, 100(2):1069-1071 (1992); Sato et al., *J. DNA Res.*, 7(1):31-63 (2000)).

Preferred amino acid biosynthetic enzymes include anthranilate synthase (U.S. Pat. No. 5,965,727; Patent Applications WO 97/26366, WO 99/11800, and WO 99/49058), tryptophan decarboxylase (Patent Application WO 99/06581), threonine decarboxylase (U.S. Pat. Nos. 5,534,421 and 5,942, 660; Patent Application WO 95/19442), threonine deaminase (Patent Applications WO 99/02656 and WO 98/55601), and aspartate kinase (U.S. Pat. Nos. 5,367,110; 5,858,749; and 6,040,160).

Preferred starch branching enzymes include those set forth in U.S. Pat. Nos. 6,232,122 and 6,147,279; and Patent Application WO 97/22703.

Alternatively, the second structural nucleic acid sequence may be designed to down-regulate a specific nucleic acid sequence. This is typically accomplished by operably linking the second structural amino acid, in an antisense orientation, with a promoter. One of ordinary skill in the art is familiar with such antisense technology. Any nucleic acid sequence may be negatively regulated in this manner. Preferable target nucleic acid sequences contain a low content of essential amino acids, yet are expressed at relatively high levels in particular tissues. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived foodstuffs, or to down-regulate catabolic enzymes involved in degradation of desired compounds such as essential amino acids.

Selectable Markers

A vector or construct may also include a selectable marker. Selectable markers may also be used to select for plants or plant cells that contain the exogenous genetic material. Examples of such include, but are not limited to: a neo gene (Potrykus et al., 1985), which codes for kanamycin resistance and can be selected for using kanamycin, RptII, G418, hpt etc.; a bar gene which codes for bialaphos resistance; a mutant EPSP synthase gene (Hinchee et al., 1988; Reynaerts et al., 1988), aadA (Jones et al., 1987) which encodes glyphosate resistance; a nitrilase gene which confers resistance to bromoxynil (Stalker et al., 1988); a mutant acetolactate synthase gene (ALS) which confers imidazolinone or sulphonylurea resistance (EP 154 204, 1985), ALS (D'Halluin et al., 1992), and a methotrexate resistant DHFR gene (Thillet et al., 1988). The selectable marker is preferably an antibiotic resistance coding sequence, or an herbicide (e.g., glyphosate) resistance coding sequence. The selectable marker is most preferably a kanamycin, hygromycin, or herbicide resistance marker.

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, 1987)); an R-locus gene, which encodes a product that regulates the production of anthocyanin pigments (red color) in plant tissues (Dellaporta et al., 1988); a β-lactamase gene (Sutcliffe et al., 1978), a gene which encodes an enzyme for which various chromogenic substrates are known (e.g., PADAC, a chromogenic cephalosporin); a luciferase gene (Ow et al., 1986); a xylE gene (Zukowsky et al., 1983) which encodes a catechol dioxygenase that can convert chromogenic catechols; an α-amylase gene (Ikatu et al., 1990); a tyrosinase gene (Katz et al., 1983) which encodes an enzyme capable of oxidizing tyrosine to DOPA and dopaquinone which in turn condenses to melanin; an α-galactosidase, which will turn a chromogenic α-galactose substrate.

Included within the term or phrase "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

Other Elements in the Recombinant Vector

Various cis-acting untranslated 5' and 3' regulatory sequences may be included in the recombinant nucleic acid vector. Any such regulatory sequences may be provided in a recombinant vector with other regulatory sequences. Such combinations can be designed or modified to produce desirable regulatory features.

A 3' non-translated region typically provides a transcriptional termination signal, and a polyadenylation signal which functions in plants to cause the addition of adenylate nucleotides to the 3' end of the mRNA. These may be obtained from the 3' regions of the nopaline synthase (nos) coding sequence, a soybean 7Sα' storage protein coding sequence, the arcelin-5 coding sequence, the albumin coding sequence, and the pea ssRUBISCO E9 coding sequence. Typically, nucleic acid sequences located a few hundred base pairs downstream of the polyadenylation site serve to terminate transcription. These regions are required for efficient polyadenylation of transcribed mRNA.

Translational enhancers may also be incorporated as part of the recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Preferred 5' nucleic acid sequences include dSSU 5', PetHSP70 5', and GmHSP17.9 5' (U.S. Pat. No. 5,362,865).

The recombinant vector may further comprise a nucleic acid sequence encoding a transit peptide. This peptide may be useful for directing a protein to the extracellular space, a plastid, or to some other compartment inside or outside of the cell. (see, e.g., EP 0 218 571, U.S. Pat. Nos. 4,940,835; 5,88,624; 5,610,041; 5,618,988; and 6,107,060).

The structural nucleic acid sequence in the recombinant vector may comprise introns. The introns may be heterologous with respect to the structural nucleic acid sequence. Preferred introns include the rice actin intron and the corn HSP70 intron for monocotyledon plants and pea rbcS3A intron 1 and petunia SSU301 introns for dicotyledon plants.

Fusion Proteins

Any of the above described structural nucleic acid sequences, and modified forms thereof, may be linked with additional nucleic acid sequences to encode fusion proteins. The additional nucleic acid sequence preferably encodes at least 1 amino acid, peptide, or protein. Many possible fusion combinations exist.

For instance, the fusion protein may provide a "tagged" epitope to facilitate detection of the fusion protein, such as GST, GFP, FLAG, or polyHIS. Such fusions preferably encode between 1 and 50 amino acids, more preferably between 5 and 30 additional amino acids, and even more preferably between 5 and 20 amino acids.

Alternatively, the fusion may provide regulatory, enzymatic, cell signaling, or intercellular transport functions. For example, a sequence encoding a plastid transit peptide may be added to direct a fusion protein to the chloroplasts within seeds. Such fusion partners preferably encode between 1 and 1000 additional amino acids, more preferably between 5 and 500 additional amino acids, and even more preferably between 10 and 250 amino acids.

Sequence Analysis

In the present invention, sequence similarity or identity is preferably determined using the "Best Fit" or "Gap" programs of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences. Optimal alignments are found by inserting gaps to maximize the number of matches using the local homology algorithm of Smith and Waterman (Smith and Waterman, 1981; Smith et al., 1983).

The Sequence Analysis Software Package described above contains a number of other useful sequence analysis tools for identifying homologues of the presently disclosed nucleotide and amino acid sequences. For example, the "BLAST" program searches for sequences similar to a query sequence (either peptide or nucleic acid) in a specified database (e.g., sequence databases maintained at the National Center for Biotechnology Information (NCBI) in Bethesda, Md.); "FastA" (Lipman and Pearson, 1985; see also, Pearson and Lipman, 1988; Pearson, 1990) performs a Pearson and Lipman search for similarity between a query sequence and a group of sequences of the same type (nucleic acid or protein); "TfastA" performs a Pearson and Lipman search for similarity between a protein query sequence and any group of nucleotide sequences (it translates the nucleotide sequences in all six reading frames before performing the comparison); "FastX" performs a Pearson and Lipman search for similarity between a nucleotide query sequence and a group of protein sequences, taking frameshifts into account. "TfastX" performs a Pearson and Lipman search for similarity between a protein query sequence and any group of nucleotide sequences, taking frameshifts into account (it translates both strands of the nucleic acid sequence before performing the comparison).

Probes and Primers

Short nucleic acid sequences having the ability to specifically hybridize to complementary nucleic acid sequences may be produced and utilized in the present invention. Such short nucleic acid molecules may be used as probes to identify the presence of a complementary nucleic acid sequence in a given sample. Thus, by constructing a nucleic acid probe which is complementary to a small portion of a particular nucleic acid sequence, the presence of that nucleic acid sequence may be detected and assessed.

Alternatively, the short nucleic acid sequences may be used as oligonucleotide primers to amplify or mutate a complementary nucleic acid sequence using PCR technology. These primers may also facilitate the amplification of related complementary nucleic acid sequences (e.g., related nucleic acid sequences from other species).

Short nucleic acid sequences may be used as primers and specifically as PCR primers. A PCR probe is a nucleic acid molecule capable of initiating a polymerase activity while in a double-stranded structure with another nucleic acid. Various methods for determining the structure of PCR primers and PCR techniques exist in the art. Computer generated searches using programs such as Primer3 (www.genome.wi.mit.edu/cgi-bin/primer/primer3.cgi), STSPipeline (www-genome.wi.mit.edu/cgi-bin/www.STS_Pipeline), or GeneUp (Pesole et al., 1998), for example, can be used to identify potential PCR primers.

Any of the nucleic acid sequences disclosed herein may be used as a primer or probe. Use of these probes or primers may greatly facilitate the identification of transgenic plants which contain the presently disclosed promoters and structural nucleic acid sequences. Such probes or primers may also be used to screen cDNA or genomic libraries for additional nucleic acid sequences related to or sharing homology with the presently disclosed promoters and structural nucleic acid sequences.

A primer or probe is generally complementary to a portion of a nucleic acid sequence that is to be identified, amplified, or mutated and of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long.

The primer or probe may, for example without limitation, be prepared by direct chemical synthesis, by PCR (U.S. Pat. Nos. 4,683,195 and 4,683,202), or by excising the nucleic acid specific fragment from a larger nucleic acid molecule.

Transgenic Plants and Transformed Plant Host Cells

The invention is also directed to transgenic plants and transformed host cells which comprise a promoter operably linked to a heterologous structural nucleic acid sequence. Other nucleic acid sequences may also be introduced into the plant or host cell along with the promoter and structural nucleic acid sequence. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

In a further embodiment of the present invention, any of the promoter sequences described herein can be used to express genes that improve the overall seedling vigor of a plant. In a preferred embodiment, a plant of the present invention that has improved seedling vigor comprises SEQ ID NOs: 1 or 2. As used herein, a seedling having "improved overall seedling vigor" means a seedling that has improved vigor relative to a plant with a similar genetic background that lacks a promoter sequence of the present invention.

In a further embodiment of the present invention, any of the promoter sequences described herein can be used to express genes that improve the growth rate of a seedling plant. In a preferred embodiment, a plant of the present invention that has improved seedling growth rate comprises SEQ ID NOs: 1 or 2. As used herein, a seedling having "improved growth rate" means a seedling that has grows at a faster pace relative to a plant with a similar genetic background at the same stage of growth that lacks a promoter sequence of the present invention.

In a further embodiment of the present invention, any of the promoter sequences described herein can be used to express genes that lengthen the period during which a plant fills its seeds. In a preferred embodiment, seed fill comprises pod fill in soybean plants or kernel filling in corn.

In another embodiment of the present invention, any of the promoter sequences described herein can be used to express genes that alter the sink strength regulation of a plant in order to enhance the rate of grain fill in seed. As used herein, to "alter" sink strength regulation of a plant means to increase or decrease the sink strength regulation of a plant relative to a plant having a similar genetic background that lacks a promoter of the present invention.

In yet another embodiment of the present invention, any of the promoter sequences described herein can be used to express genes that regulate or enhance seed viability or seed storage, thereby improving stand count or yield or both.

In a preferred embodiment, the transgenic plants and transformed host cells comprise a seed promoter. In a most preferred embodiment, the transgenic plants and transformed host cells comprise any nucleic acid molecule of the present invention as described herein, including a nucleic acid sequence selected from the group consisting of SEQ ID NOs: 1-4, and complements thereof.

In a particularly preferred embodiment, the transgenic plant of the present invention is a soybean plant. In a preferred embodiment, a soybean plant of the present invention comprises one or more introduced nucleic acid molecules of the present invention. In a preferred embodiment, a transformed soybean plant of the present invention comprises a nucleic acid molecule selected from the group consisting of SEQ ID NOs: 1-4. In a preferred embodiment a transformed soybean plant of the present invention comprises a nucleic acid molecule comprising SEQ ID NO: 1.

Means for preparing such recombinant vectors are well known in the art. For example, methods for making recombinant vectors particularly suited to plant transformation are described in U.S. Pat. Nos. 4,971,908; 4,940,835; 4,769,061; and 4,757,011. These vectors have also been reviewed (Rodriguez et al., 1988; Glick et al., 1993).

Typical vectors useful for expression of nucleic acids in cells and higher plants are well known in the art and include vectors derived from the tumor-inducing (Ti) plasmid of *Agrobacterium tumefaciens* (Rogers et al., 1987). Other recombinant vectors useful for plant transformation have also been described (Fromm et al., 1985). Elements of such recombinant vectors include, without limitation, those discussed above.

A transformed host cell may generally be any cell that is compatible with the present invention. A transformed host plant or cell can be or derived from a monocotyledonous plant or a dicotyledonous plant including, but not limited to canola, *crambe*, maize, mustard, castor bean, sesame, cottonseed, linseed, soybean, *Arabidopsis phaseolus*, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris, Brassica napus*, turfgrass, sugarbeet, coffee and dioscorea (Christou, In: *Particle Bombardment for Genetic Engineering of plants*, Biotechnology Intelligence Unit, Academic Press, San Diego, Calif. (1996)), with canola, maize, *Brassica campestris, Brassica napus*, rapeseed, soybean, safflower, wheat, rice and sunflower preferred, and canola, rapeseed, maize, *Brassica campestris, Brassica napus*, soybean, sunflower, safflower, oil palms, and peanut more preferred. In a particularly preferred embodiment, the plant or cell is or derived from canola. In another particularly preferred embodiment, the plant or cell is or derived from *Brassica napus*. In another particularly preferred embodiment, the plant or cell is or derived from soybean.

The soybean cell or plant is preferably an elite soybean cell line. An "elite line" is any commercially available line that has resulted from breeding and selection for superior agronomic performance. Examples of elite lines, include without limitation, the following: HARTZ™ variety H4994, HARTZ™ variety H5218, HARTZ™ variety H5350, HARTZ™ variety H5545, HARTZ™ variety H5050, HARTZ™ variety H5454, HARTZ™ variety H5233, HARTZ™ variety H5488, HARTZ™ variety HLA572, HARTZ™ variety H6200, HARTZ™ variety H6104, HARTZ™ variety H6255, HARTZ™ variety H6586, HARTZ™ variety H6191, HARTZ™ variety H7440, HARTZ™ variety H4452 Roundup Ready™, HARTZ™ variety H4994 Roundup Ready™, HARTZ™ variety H4988 Roundup Ready™, HARTZ™ variety H5000 Roundup Ready™, HARTZ™ variety H5147 Roundup Ready™, HARTZ™ variety H5247 Roundup Ready™, HARTZ™ variety H5350 Roundup Ready™, HARTZ™ variety H5545 Roundup Ready™, HARTZ™ variety H5855 Roundup Ready™, HARTZ™ variety H5088 Roundup Ready™, HARTZ™ variety H5164 Roundup Ready™, HARTZ™ variety H5361 Roundup Ready™, HARTZ™ variety H5566 Roundup Ready™, HARTZ™ variety H5181 Roundup Ready™, HARTZ™ variety H15889 Roundup Ready™, HARTZ™ variety H5999 Roundup Ready™, HARTZ™ variety H6013 Roundup Ready™, HARTZ™ variety H6255 Roundup Ready™, HARTZ™ variety H6454 Roundup Ready™, HARTZ™ variety H6686 Roundup Ready™, HARTZ™ variety H7152 Roundup Ready™, HARTZ™ variety H7550 Roundup Ready™, HARTZ™ variety H8001 Roundup Ready™ (HARTZ SEED, Stuttgart, AR); A0868, AG0901, A1553, A1900, AG1901, A1923, A2069, AG2101, AG2201, A2247, AG2301, A2304, A2396, AG2401, AG2501, A2506, A2553, AG2701, AG2702, A2704, A2833, A2869, AG2901, AG2902, AG3001, AG3002, A3204, A3237, A3244, AG3301, AG3302, A3404, A3469, AG3502, A3559, AG3601, AG3701, AG3704, AG3750, A3834, AG3901, A3904, A4045 AG4301, A4341, AG4401, AG4501, AG4601, AG4602, A4604, AG4702, AG4901, A4922, AG5401, A5547, AG5602, A5704, AG5801, AG5901, A5944, A5959, AG6101, QR4459 and QP4544 (Asgrow Seeds, Des Moines, Iowa); DeKalb variety CX445 (DeKalb, IL).

The invention is also directed to a method of producing transformed plants which comprise, in a 5' to 3' orientation, a promoter operably linked to a heterologous structural nucleic acid sequence. Other sequences may also be introduced into plants along with the promoter and structural nucleic acid sequence. These other sequences may include 3' transcriptional terminators, 3' polyadenylation signals, other untranslated sequences, transit or targeting sequences, selectable markers, enhancers, and operators. Preferred recombinant vectors, structural nucleic acid sequences, promoters, and other regulatory elements including, without limitation, those described herein.

The method generally comprises the steps of selecting a suitable plant, transforming the plant with a recombinant vector, and obtaining the transformed host cell.

There are many methods for introducing nucleic acids into plants. Suitable methods include bacterial infection (e.g., *Agrobacterium*), binary bacterial artificial chromosome vectors, direct delivery of nucleic acids (e.g., via PEG-mediated transformation, desiccation/inhibition-mediated nucleic acid uptake, electroporation, agitation with silicon carbide fibers, and acceleration of nucleic acid coated particles, etc. (reviewed in Potrykus et al., 1991)).

Technology for introduction of nucleic acids into cells is well known to those of skill in the art. Methods can generally be classified into four categories: (1) chemical methods (Graham and van der Eb, 1973; Zatloukal et al., 1992); (2) physical methods such as microinjection (Capecchi, 1980), electroporation (Wong and Neumann, 1982; Froman et al., 1985; U.S. Pat. No. 5,384,253), and particle acceleration (Johnston and Tang, 1994; Fynan et al., 1993); (3) viral vectors (Clapp, 1993; Lu et al., 1993; Eglitis and Anderson, 1988); and (4) receptor-mediated mechanisms (Curiel et al., 1992; Wagner et al., 1992). Alternatively, nucleic acids can be directly introduced into pollen by directly injecting a plant's reproductive organs (Zhou et al, 1983; Hess, 1987; Luo et al., 1988; Pena et al., 1987). In another aspect nucleic acids may also be injected into immature embryos (Neuhaus et al., 1987).

Regeneration, development, and cultivation of plants from transformed plant protoplast or explants is taught in the art (Weissbach and Weissbach, 1988; Horsch et al., 1985). Transformants are generally cultured in the presence of a selective media which selects for the successfully transformed cells and induces the regeneration of plant shoots (Fraley et al., 1983). Such shoots are typically obtained within two to four months.

Shoots are then transferred to an appropriate root-inducing medium containing the selective agent and an antibiotic to prevent bacterial growth. Many of the shoots will develop roots. These are then transplanted to soil or other media to allow the continued development of roots. The method, as outlined, will generally vary depending on the particular plant employed.

Preferably, the regenerated transgenic plants are self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

A transgenic plant may pass along the nucleic acid sequence encoding the enhanced gene expression to its progeny. The transgenic plant is preferably homozygous for the nucleic acid encoding the enhanced gene expression and transmits that sequence to all of its offspring upon as a result of sexual reproduction. Progeny may be grown from seeds produced by the transgenic plant. These additional plants may then be self-pollinated to generate a true breeding line of plants.

The progeny from these plants are evaluated, among other things, for gene expression. The gene expression may be detected by several common methods such as western blotting, northern blotting, immunoprecipitation, and ELISA.

Plants or agents of the present invention can be utilized in methods, for example without limitation, to obtain a seed that expresses a structural nucleic acid molecule in that seed, to obtain a seed enhanced in a product of a structural gene, to obtain meal enhanced in a product of a structural gene, to obtain feedstock enhanced in a product of a structural gene, and to obtain oil enhanced in a product of a structural gene Plants utilized in such methods may be processed. A plant or plant part may be separated or isolated from other plant parts. A preferred plant part for this purpose is a seed. It is understood that even after separation or isolation from other plant parts, the isolated or separated plant part may be contaminated with other plant parts. In a preferred aspect, the separated plant part is greater than 50% (w/w) of the separated material, more preferably, greater than 75% (w/w) of the separated material, and even more preferably greater than 90% (w/w) of the separated material. Plants or plant parts of the present invention generated by such methods may be processed into products using known techniques. Preferred products are meal, feedstock and oil.

Feed, Meal, Protein and Oil Preparations

Any of the plants or parts thereof of the present invention may be processed to produce a feed, meal, protein or oil preparation. A particularly preferred plant part for this purpose is a seed. In a preferred embodiment the feed, meal, protein or oil preparation is designed for ruminant animals. Methods to produce feed, meal, protein and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the protein preparation is a high protein preparation. Such a high protein preparation preferably has a protein content of greater than 5% w/v, more preferably 10% w/v, and even more preferably 15% w/v. In a preferred oil preparation, the oil preparation is a high oil preparation with an oil content derived from a plant or part thereof of the present invention of greater than about 5% w/v, more preferably greater than about 10% w/v, and even more preferably greater than about 15% w/v. In a preferred embodiment the oil preparation is a liquid and of a volume greater than about 1, about 5, about 10, or about 50 liters. The present invention provides for oil produced from plants of the present invention or generated by a method of the present invention. Such oil may be a minor or major component of any resultant product. Moreover, such oil may be blended with other oils. In a preferred embodiment, the oil produced from plants of the present invention or generated by a method of the present invention constitutes greater than about 0.5%, about 1%, about 5%, about 10%, about 25%, about 50%, about 75%, or about 90% by volume or weight of the oil component of any product. In another embodiment, the oil preparation may be blended and can constitute greater than about 10%, about 25%, about 35%, about 50%, or about 75% of the blend by volume. Oil produced from a plant of the present invention can be admixed with one or more organic solvents or petroleum distillates.

In a further embodiment, meal of the present invention may be blended with other meals. In a preferred embodiment, the meal produced from plants of the present invention or generated by a method of the present invention constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

Seed Containers

Seeds of the plants may be placed into a container. As used herein, a container is any object capable of holding such seeds. A container preferably contains greater than about 500, about 1,000, about 5,000, or about 25,000 seeds where at least about 10%, about 25%, about 50%, about 75%, or about 100% of the seeds are derived from a plant of the present invention.

Breeding Programs

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability and the like will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g., Fehr, *Principles of Cultivar Development*, Vol. 1, pp. 2-3 (1987)).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636.

EXAMPLES

The following examples are provided and should not be interpreted in any way to limit the scope of the present invention.

Example 1

The promoter for the soybean lea9 gene (Hsing, et al., *Plant Physiol.*, 100:2121-2122 (1992)) is PCR amplified from soybean genomic DNA (cv. Asgrow 4922) using the following primers based on the published sequence:

```
Primer ID lea9-5'
5'-ACCTGCGGCCGCCAGTACTTACGCCACACCAA    (SEQ ID NO: 5)
CTTAC-3';
and Primer ID lea9-3'
5'-GCAGCTGTTTCCTTGATGGACTCTC-3'.       (SEQ ID NO: 6)
```

All oligonucleotide primers are obtained from Gibco Life Technologies (Grand Island, N.Y.). The initial PCR reaction is performed using the Taq DNA polymerase kit (Boehringer Mannheim, Germany). The nested PCR reaction follows the primary PCR reaction, using the 5' primer of the initial reaction and lea9-3'nest' (GAAGATCTCCTGCAATTTCAAAGATCAATTATTTCC) (SEQ ID NO: 7). The following tables summarize the components used for these reactions:

| INITIAL PCR REACTION | |
|---|---|
| Component | Amount |
| Soybean Genomic DNA (80 ng/µl) | 1.0 µl |
| dNTP mix (10 mM of each dNTP) | 1.0 µl |
| Primer lea9-5' (10 µM) | 1.0 µl |
| Primer lea9-3' (10 µM) | 1.0 µl |
| 10X PCR Buffer (containing MgCl$_2$) | 5 µl (final conc of 1X) |
| Taq Polymerase | 1.0 µl |
| Distilled Water | bring to 50 µl final volume |

| NESTED PCR REACTIONS | |
|---|---|
| Component | Amount |
| aliquot from primary PCR reaction | 1.0 µl |
| dNTP mix (10 mM of each dNTP) | 1.0 µl |
| Primer lea9-5' (10 µM) | 1.0 µl |
| Primer lea9-3'nest' (10 µM) | 1.0 µl |
| 10X PCR Buffer (containing MgCl$_2$) | 5 µl (final conc of 1X) |
| Taq polymerase | 1.0 µl |
| Distilled Water | bring to 50 µl final volume |

The reactions are heated to 95° C. before adding the polymerase enzyme. Both the initial and nested PCR reactions are initiated by denaturing the sample at 94° C. for 2 minutes. The reaction mixture is incubated for 7 cycles consisting of 94° C. for 30 seconds, 72° C. for 2.5 minutes (−1° C./cycle). The reaction mixture is then incubated for 30 cycles consisting of 94° C. for 30 seconds, 68° C. for 2 minutes, 72° C. for 2 seconds minutes with a final step of 72° C. for 10 minutes. The reactions are held at 4° C. until next step.

Figure 2:
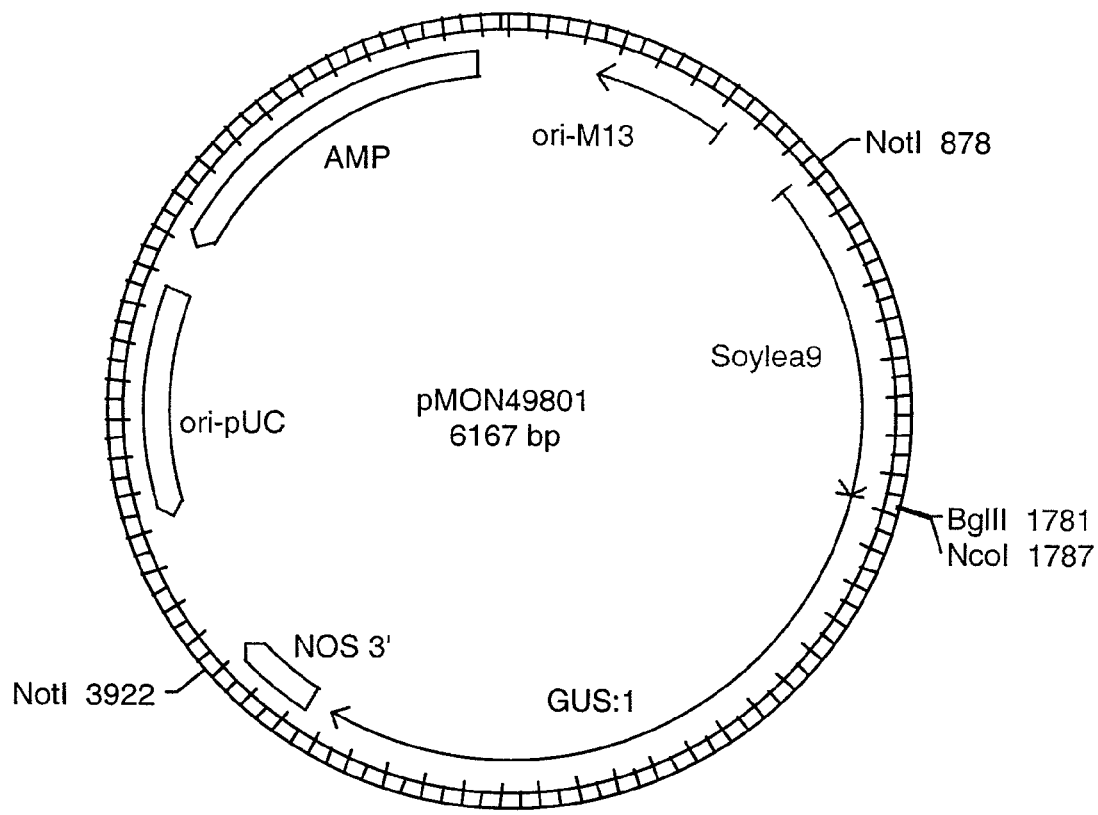
FIG. 2 is a schematic representation of pMON49801.

The product from the nested PCR reaction is purified by agarose gel electrophoresis using the Qiagen Gel Extraction Kit (Qiagen, Valencia, Calif.; product Cat#28704). An aliquot of the purified PCR product is then digested with the restriction enzymes NotI and BglII (Promega, Madison, Wis.) and ligated into a pMON8677 (FIG. 1) backbone, which is also cut with NotI and BglII, to remove the e35S promoter cassette. The ligation is performed with the Rapid DNA Ligation Kit from Boehringer-Mannheim (Germany, catalog number Cat#1635379) according to the manufacturer's recommendations. The resulting construct in which the lea9 promoter is directly upstream of the uidA (β-glucuronidase) reporter gene is named pMON49801 (FIG. 2) and is used in transient assay analysis.

An aliquot of the ligation reaction is transformed into a suitable *E. coli* (DH5α) and the cells are plated on selection medium consisting of Luria Broth ((LB) 10% Bactotryptone, 5% yeast extract, and 10% NaCl), with 100 µg/ml ampicillin. Bacterial transformants are selected, grown in liquid culture, and the plasmid DNA is isolated using the Qiaprep Spin Miniprep Kit (Qiagen Corp., Valencia, Calif.). Purified plas-

Example 2

The promoter for the *Arabidopsis thaliana* per1 gene (Haslekas, et al., *Plant Mol. Biol.* 36:833-845 (1998)) is PCR amplified from *Arabidopsis* (cv. Columbia) genomic DNA using the following primers designed from the published gene sequence:

```
Primer ID JA44
5'-GGATCCAAATCAAAGTTTAATAGACTT-3';    (SEQ ID NO: 8)
and

Primer ID JA46
5'-TCTAGGTTCGGCACCGTGTCTC-3'.         (SEQ ID NO: 9)
```

The oligonucleotide primers are supplied by Gibco Life Technologies (Grand Island, N.Y.). The PCR is performed with the Expand High Fidelity PCR System (Boehringer Mannheim, (Germany), catalog number 1732641). Following the primary PCR reaction, a second reaction using nested PCR primers is performed using 1 μl of product from the primary reaction and the following primers designed from the published sequence:

```
Primer ID JA45
5'-TAGCGGCCGCTAATAGACTTTGCACCTCCA    (SEQ ID NO: 10)
T-3';
and Primer ID JA47
5'-AACCATGGTTTACCTTTTATATTTATATATA    (SEQ ID NO: 11)
GAA-3'.
```

The PCR components and conditions are outlined below:

| Primary PCR | |
| --- | --- |
| Component | Amount |
| *Arabidopsis* Genomic DNA | 0.5 μl (0.75 ug) |
| dNTP mix (10 mM of each dNTP) | 2.0 μl |
| Primer JA44 (10 μM) | 3.0 μl |
| Primer JA46 (10 μM) | 3.0 μl |
| 10X PCR Buffer (containing MgCl$_2$) | 10 μl (final conc of 1X) |
| Polymerase enzyme | 0.75 μl |
| Distilled Water | bring to 100 μl final volume |

| NESTED PCR | |
| --- | --- |
| Component | Amount |
| aliquot from primary PCR reaction | 1.0 μl |
| dNTP mix (10 mM of each dNTP) | 2.0 μl |
| Primer JA45 (10 μM) | 3.0 μl |
| Primer JA47 (10 μM) | 3.0 μl |
| 10X PCR Buffer (containing MgCl$_2$) | 10 μl (final conc of 1X) |
| Polymerase enzyme | 0.75 μl |
| Distilled Water | bring to 100 μl final volume |

The reactions are heated to 95° C. before adding the polymerase enzyme. Both the initial and nested PCR reactions are initiated by denaturing the sample at 94° C. for 2 minutes. The reaction mixture is incubated for 10 cycles consisting of 94° C. for 15 seconds, 60° C. for 30 seconds and 72° C. for 90 seconds. The reaction mixture is then incubated for 26 cycles consisting of 94° C. for 15 seconds, 60° C. for 30 seconds, 72° C. for 30 seconds for the initial cycle and 50 seconds for each additional cycle with a final step of 72° C. for 7 minutes. The reactions are held at 4° C. until next step.

Figure 3:
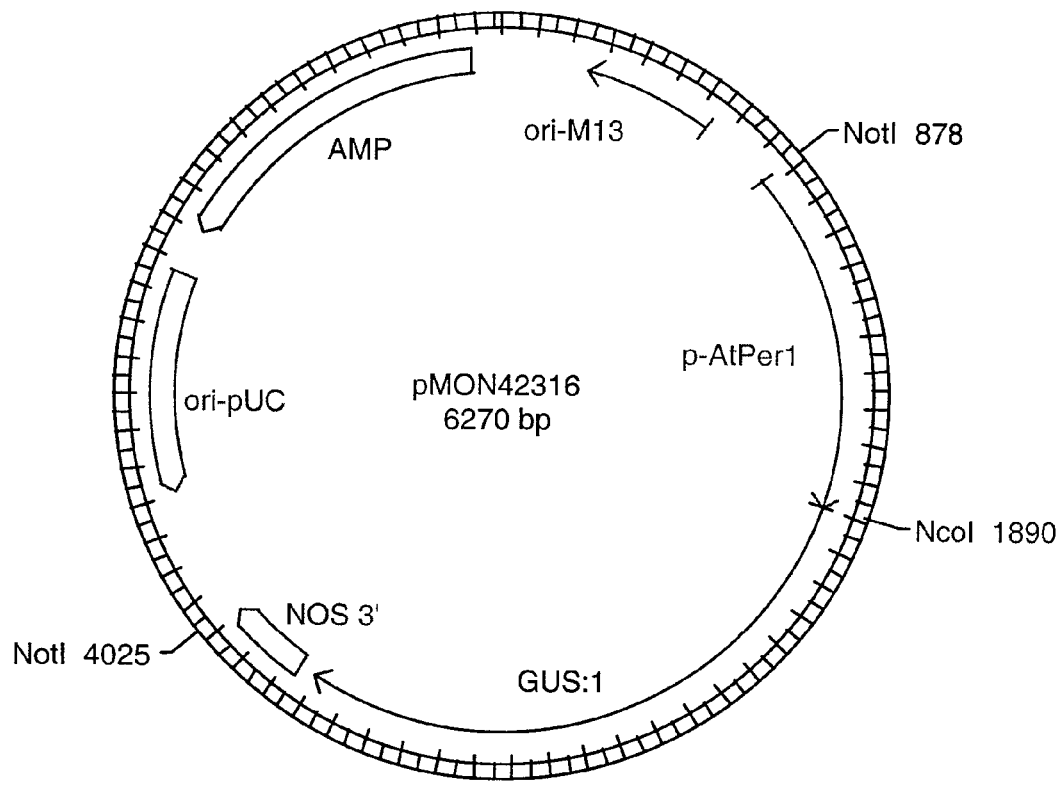
FIG. 3 is a schematic representation of pMON42316.

A 25 μl aliquot of the PCR product is taken for agarose gel analysis. The remaining PCR product is purified using the Qiagen PCR Purification Kit (Qiagen, Inc., Valencia, Calif., product number 28104) following the conditions recommended by the manufacturer. An aliquot of the purified PCR product is then digested with restriction enzymes NotI and NcoI (Promega, Madison, Wis.) and ligated into a pMON8677 backbone (FIG. 1), which had been cut with NotI and NcoI to remove the e35S promoter cassette. The ligation is performed with the Rapid DNA Ligation Kit from Boehringer-Mannheim (Germany, catalog number 1635379) according to the manufacturer's recommendations. The resulting construct is named pMON42316 (FIG. 3) in which the AtPer1 promoter is directly upstream of the uidA (β-glucuronidase) reporter gene.

An aliquot of the ligation reaction is transformed into a suitable *E. coli* host (DH5α) and the cells plated on selection medium (LB with 100 ug/ml carbenicillin). Bacterial transformants are selected, grown in liquid culture (LB with 100 ug/ml carbenicillin), and the plasmid DNA is isolated using the Qiaprep Spin Miniprep Kit (Qiagen Corp., Valencia, Calif.). Purified plasmid containing the predicted insert size based on restriction enzyme analysis are sequenced using primers JA45, JA47, and a primer named GUS 5'-2, 5'-GTAACGCGCTTTCCCACCAACGCT (SEQ ID NO: 12), which anneals in the GUS coding region of the plasmid. The sequence of the cloned AtPer1 promoter matches that of the published promoter sequence.

Example 3

The promoter for the soybean Sle2 gene (Calvo, et al., *Theor. Appl. Genet.*, 94:957-967 (1997)) is amplified from the a soybean genomic DNA library (cv. Williams 82, purchased from Stratagene, La Jolla, Calif.; cat. number 946103). The following primers, which are designed from the published gene sequence, are used for the primary reaction:

```
Primer ID JA41
5'-GTGTTACATTATCACTTATCCTGGTC-3';    (SEQ ID NO: 13)
and

Primer ID Jeahre2
5'-GCTCAATTAACCCTCACTAAAGGGA-3'.     (SEQ ID NO: 14)
```

The oligonucleotide primers are supplied by Gibco Life Technologies (Grand Island, N.Y.). The primary PCR reaction is performed with the Expand Long Template PCR system (Boehringer Mannheim, Germany, catalog number 1681834).

Following the primary PCR reaction, a nested PCR reaction is performed using 1 μl of product from the primary reaction as template DNA and the following nested primers designed from the published sequence:

```
Primer ID JA43
5'-CTCTTGAGCACGTTCTTCTCCT-3';        (SEQ ID NO: 15)
and

Primer ID Jeahre2
5'-GCTCAATTAACCCTCACTAAAGGGA-3'.     (SEQ ID NO: 16)
```

The PCR components and conditions for both reactions are outlined below:

Primary PCR (Long Template PCR Kit)

| Component | Amount |
|---|---|
| Soybean Genomic DNA | 1.0 µl |
| dNTP mix (10 mM of each dNTP) | 2.5 µl |
| Primer JA41 (10 µM) | 1.0 µl |
| Primer Jeahre2 (10 µM) | 1.0 µl |
| 10X PCR Buffer #3 (containing MgCl$_2$) | 5 µl (final conc of 1X) |
| Polymerase enzyme mix | 0.75 µl |
| Distilled Water | bring to 50 µl final volume |

Nested PCR (long template PCR kit)

| Component | Amount |
|---|---|
| aliquot from primary PCR reaction | 1.0 µl |
| dNTP mix (10 mM of each dNTP) | 2.5 µl |
| Primer JA43 (10 µM) | 1.0 µl |
| Primer Jeahre2 (10 µM) | 1.0 µl |
| 10X PCR Buffer #3(containing MgCl$_2$) | 5 µl (final conc of 1X) |
| Polymerase enzyme mix | 0.75 µl |
| Distilled Water | bring to 50 µl final volume |

Both the primary and nested PCR reactions are initiated by denaturing the sample at 94° C. for 2 minutes. The reaction mixture is incubated for 10 cycles consisting of 94° C. for 10 seconds, 69° C. for 30 seconds (−1.5° C./cycle), and 68° C. for 12 minutes. The reaction mixture is then incubated for 25 cycles consisting of 94° C. for 10 seconds, 58° C. for 30 seconds, 68° C. for 12 minutes, and a final step of 68° C. for 7 minutes. The reactions are held at 4° C. until the next step. After successful cloning and identification of the Sle2 promoter region, the promoter is re-amplified with the Expand High Fidelity PCR System (Boehringer Mannheim, Germany, catalog number 1732641) using the following primers:

```
Primer ID JA53
5'-GTGCGGCCGCACTCAAAGTTTATTGAGTTTA (SEQ ID NO: 17)
CTTAGAG-3';
and Primer ID JA54
5'-ACAGATCTGTTTCTCACACTTGCAAAATTCT (SEQ ID NO: 18)
CTC-3'.
```

This third reaction is done to add the NotI and BglII restriction sites to the 5' and 3' ends of the clone, respectively.

Following the reactions, a 25 µl aliquot of the High Fidelity PCR product is taken for agarose gel analysis. The band in the gel matched the expected size (~1.3 kb) and is purified following the procedure detailed in the Qiagen Gel Extraction Kit (Qiagen, Valencia, Calif.; product #28704). An aliquot of the purified PCR product is then digested with restriction enzymes NotI and BglII (Promega, Madison, Wis.) and ligated into a pMON8677 backbone (FIG. 1), which has been cut with NotI and BglII to remove the e35S promoter cassette. The ligation is then performed with the Rapid DNA Ligation Kit from Boehringer-Mannheim (Germany, catalog number 1635379) according to the manufacturer's recommendations.

Figure 4:
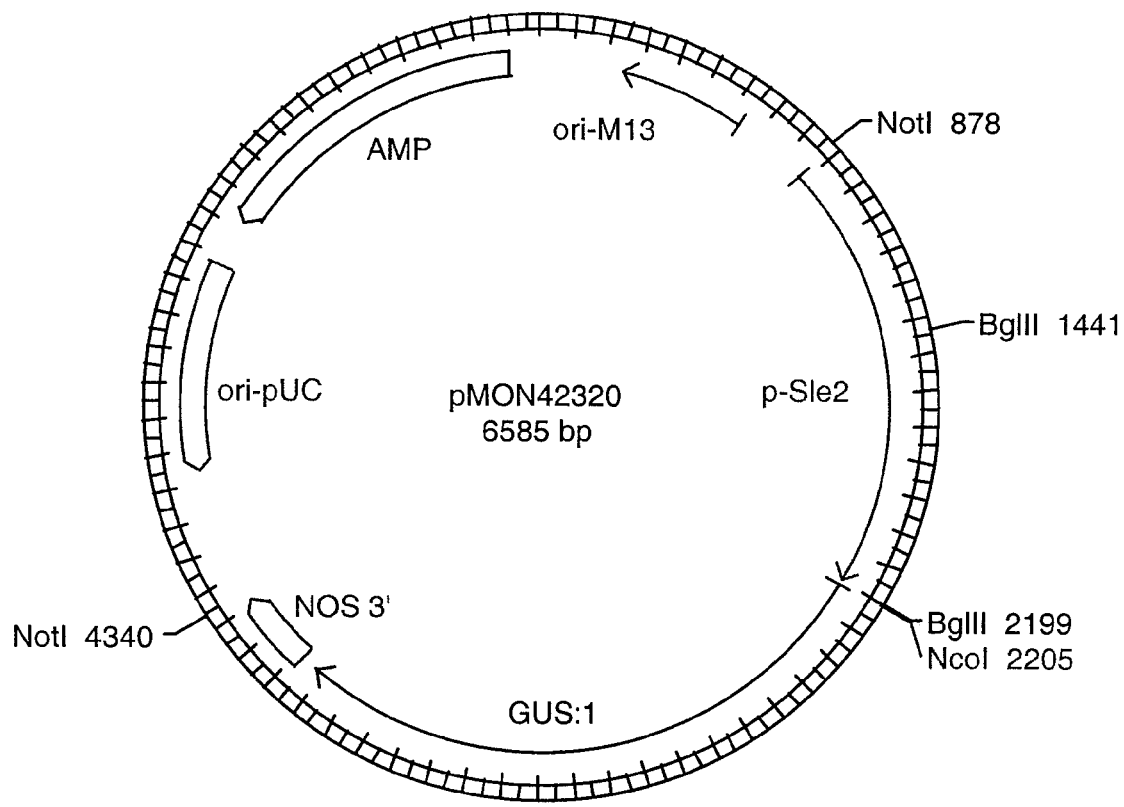
FIG. 4 is a schematic representation of pMON42320.

The resulting construct, named pMON42320 (FIG. 4), had the Sle2 promoter directly upstream of the uidA (β-glucuronidase) reporter gene.

Bacterial transformation is done as described in example 1. Purified plasmid containing the predicted insert size based on restriction enzyme analysis is sequenced using the following primers:

```
JA51
5'-ATAGTACCCCAACACGCTAC-3';          (SEQ ID NO: 19)

JA53
5'-GTGCGGCCGCACTCAAAGTTTATTGAGTTTA  (SEQ ID NO: 20)

CTTAGAG-3';

JA54;                                 (SEQ ID NO: 18)

JA55
5'-GGAACCGAATATAATTGGCTC-3';         (SEQ ID NO: 21)
``` and the GUS5'-2 primer (SEQ ID NO: 12), which anneals in the GUS coding region of the plasmid.

Example 4

The Soybean lectin promoter is isolated from soybean genomic DNA (cv. 3237) using PCR methodology. The PCR reaction is conducted using the Expand High Fidelity PCR System (Boehringer Mannheim, Germany, catalog number Cat#1732641). The primary PCR reaction is performed using the following primers, which are based on the published sequence (Vodkin et. al., *Cell,* 34:1023-1231 (1983)).

```
Primer ID JA23
5'-GCCTTCCTGGTCAGTAGCACCAGTA-3';     [SEQ ID NO: 22]
and

Primer ID JA25
5'-CCATGCCATCGTATCGTGTCACAAT-3'.     [SEQ ID NO: 23]
```

The oligonucleotide primers are supplied by Gibco Life Technologies (Grand Island, N.Y.). Following the primary PCR reaction, a nested PCR reaction is performed using 1 µl of product from the primary reaction and the following primers:

```
Primer ID JA26
5'-AGGCGGCCGCCTGCAGATGGAATACAGCAAT  (SEQ ID NO: 24)

GAACAAATGC-3';
and

Primer ID JA28
5'-CTCCATGGAGATCTTGCTTTGCTTCAGCTAA  (SEQ ID NO: 25)

ATTGCACT-3'.
```

This reaction is done to provide added cloning sites for the restriction enzymes NotI and NcoI to the 5' and 3' ends of the cloned promoter, respectively.

The PCR components and conditions for the primary reaction are outlined below:

| PRIMARY PCR | |
| --- | --- |
| Component | Amount |
| Soybean Genomic DNA | 2.0 μl |
| dNTP mix (10 mM of each dNTP) | 1.0 μl |
| Primer JA23 (10 μM) | 1.5 μl |
| Primer JA25 (10 μM) | 1.5 μl |
| 10X PCR Buffer #3 (containing MgCl$_2$) | 5 μl (final conc of 1X) |
| Polymerase enzyme mix | 0.75 μl |
| Distilled Water | bring to 50 μl final volume |

The primary PCR reaction is initiated by denaturing the sample for 2 minutes at 94° C. The reaction mixture is incubated for ten cycles consisting of 94° C. for 15 seconds, followed by 52° C. for 30 seconds, and finally 72° C. for 1 minute. The reaction is then incubated for 20 cycles of 52° C. for 30 seconds, followed by 72° C. for 1 minute and increasing the time by 20 seconds each cycle. The reaction is then incubated at 72° C. for 7 minutes as a final extension and held at 4° C. for an extended incubation.

The PCR components and conditions for the nested PCR reaction are outlined below:

| NESTED PCR | |
| --- | --- |
| Component | Amount |
| Primary PCR product | 1.0 μl |
| dNTP mix (10 mM of each dNTP) | 1.0 μl |
| Primer JA26 (10 μM) | 1.5 μl |
| Primer JA28 (10 μM) | 1.5 μl |
| 10X PCR Buffer #3 (containing MgCl$_2$) | 5 μl (final conc of 1X) |
| Polymerase enzyme mix | 0.75 μl |
| Distilled Water | bring to 50 μl final volume |

The nested PCR reaction is initiated by denaturing the sample for 2 minutes at 94° C. The reaction mixture is incubated for ten cycles consisting of 94° C. for 15 seconds, followed by 46° C. for 30 seconds, and finally 72° C. for 1 minute. The reaction is then incubated for 20 cycles of 94° C. for 15 seconds, followed by 72° C. for 1 minute and increasing the time by 20 seconds each cycle. The reaction is then incubated at 72° C. for 7 minutes as a final extension and held at 4° C. for an extended incubation until the next step.

Figure 5:
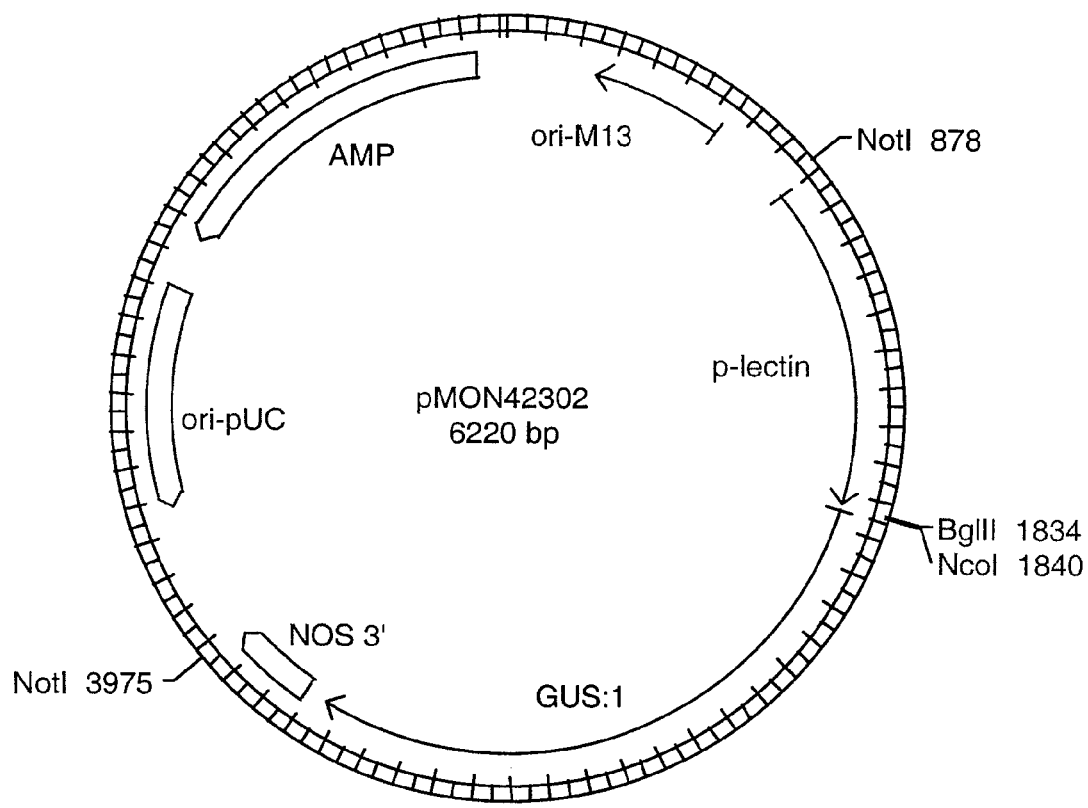
FIG. 5 is a schematic representation of pMON42302.

After nested PCR, the entire product of the High Fidelity PCR reaction is analyzed by agarose gel analysis. The 0.96 Kb band is cut out and purified using the Qiagen Gel Extraction Kit (Qiagen, Valencia, Calif.; product Cat#28704). An aliquot of the purified PCR product is then digested with restriction enzymes NotI and NcoI (Promega, Madison, Wis.) and ligated into a pMON8677 backbone (FIG. 1), which is also cut with NotI and NcoI to remove the e35S promoter cassette (NBP# 6301633). The ligation is performed with the Rapid DNA Ligation Kit (Boehringer-Mannheim, Germany, catalog number Cat#1635379) according to the manufacturer's recommendations. The resulting construct, in which the lectin promoter is directly upstream of the uidA (β-glucuronidase) reporter gene, is named pMON42302 (FIG. 5).

An aliquot of the ligation reaction is transformed into a suitable *E. coli* (DH5α) and the cells are plated on selection medium (LB with 100 μg/ml ampicillin). Bacterial transformants are selected, grown in liquid culture (LB with 100 μg/ml ampicillin), and the plasmid DNA is isolated using the Qiaprep Spin Miniprep Kit (Qiagen Corp., Valencia, Calif.). Purified plasmid containing the predicted insert size based on restriction enzyme analysis are sequenced using the dye terminator method using primers: JA26, JA28, and GUS5'-2, which anneals in the GUS coding region of the plasmid. The sequence of the cloned lectin promoter matched that of the published lectin promoter from Vodkin, et al., (1983).

Example 5

This example describes the transformation of soybean plants with heterologous genes driven by the sle2 and lectin promoters.

Vector Construction

Figure 10:
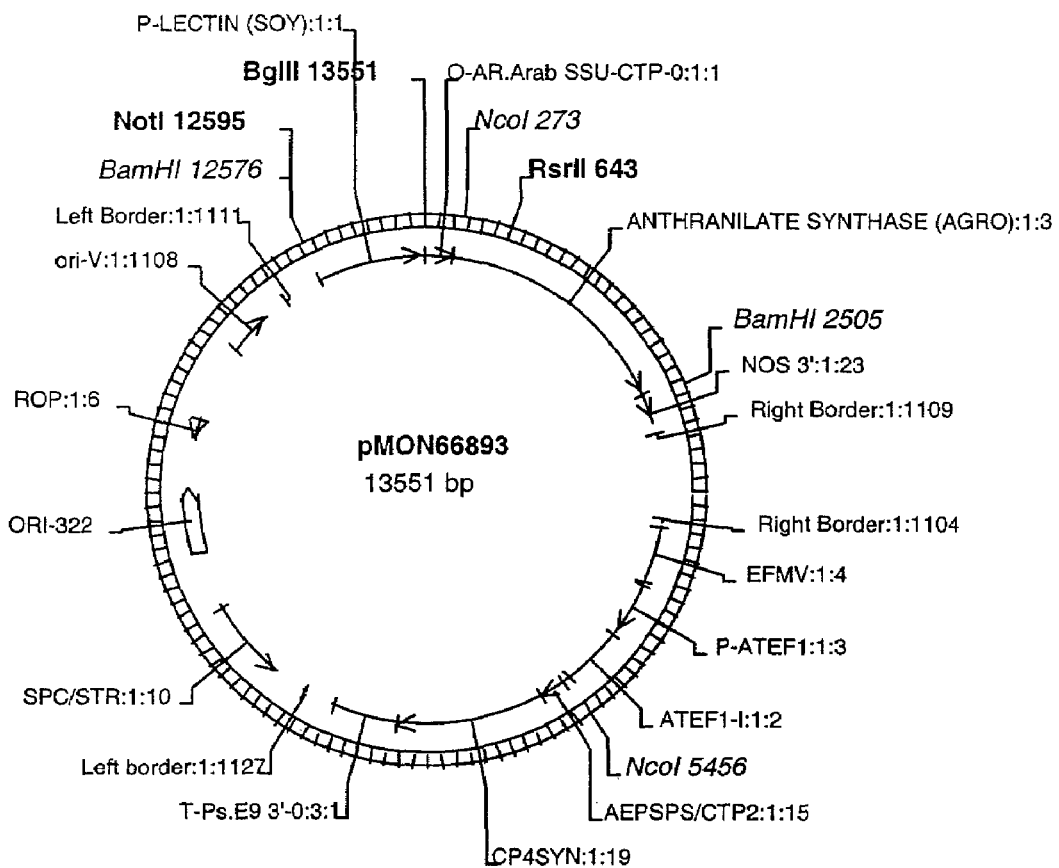
FIG. 10 is a schematic representation of pMON66893.
Figure 11:
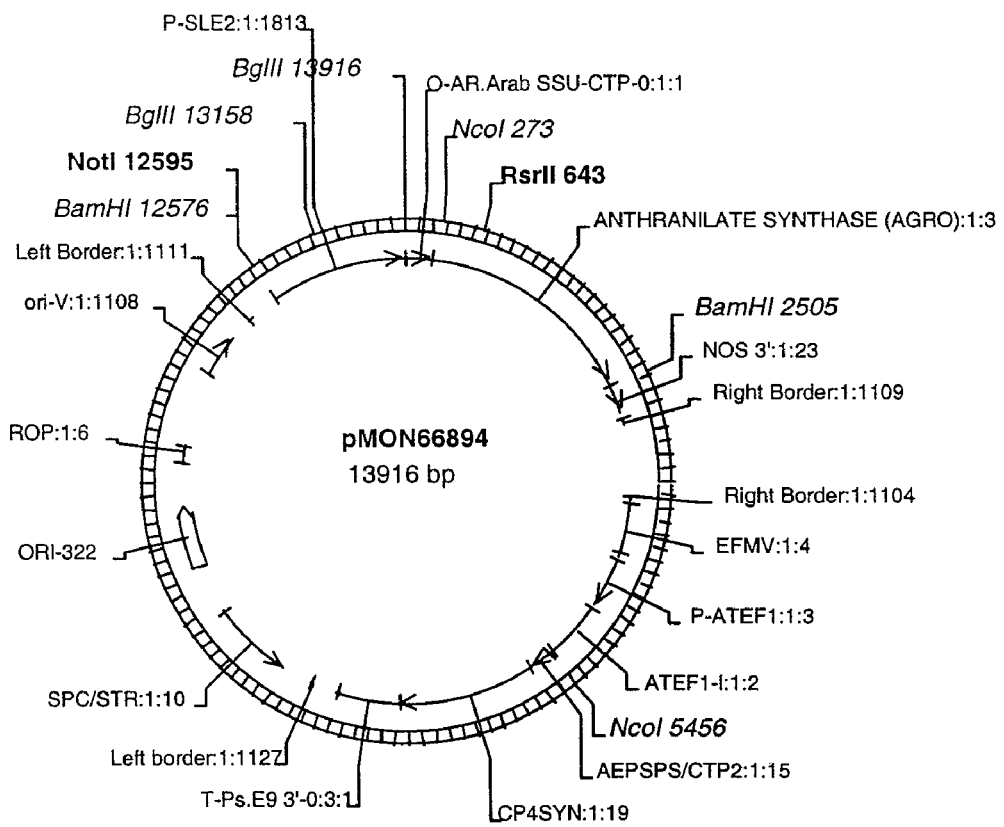
FIG. 11 is a schematic representation of pMON66894.
Figure 13:
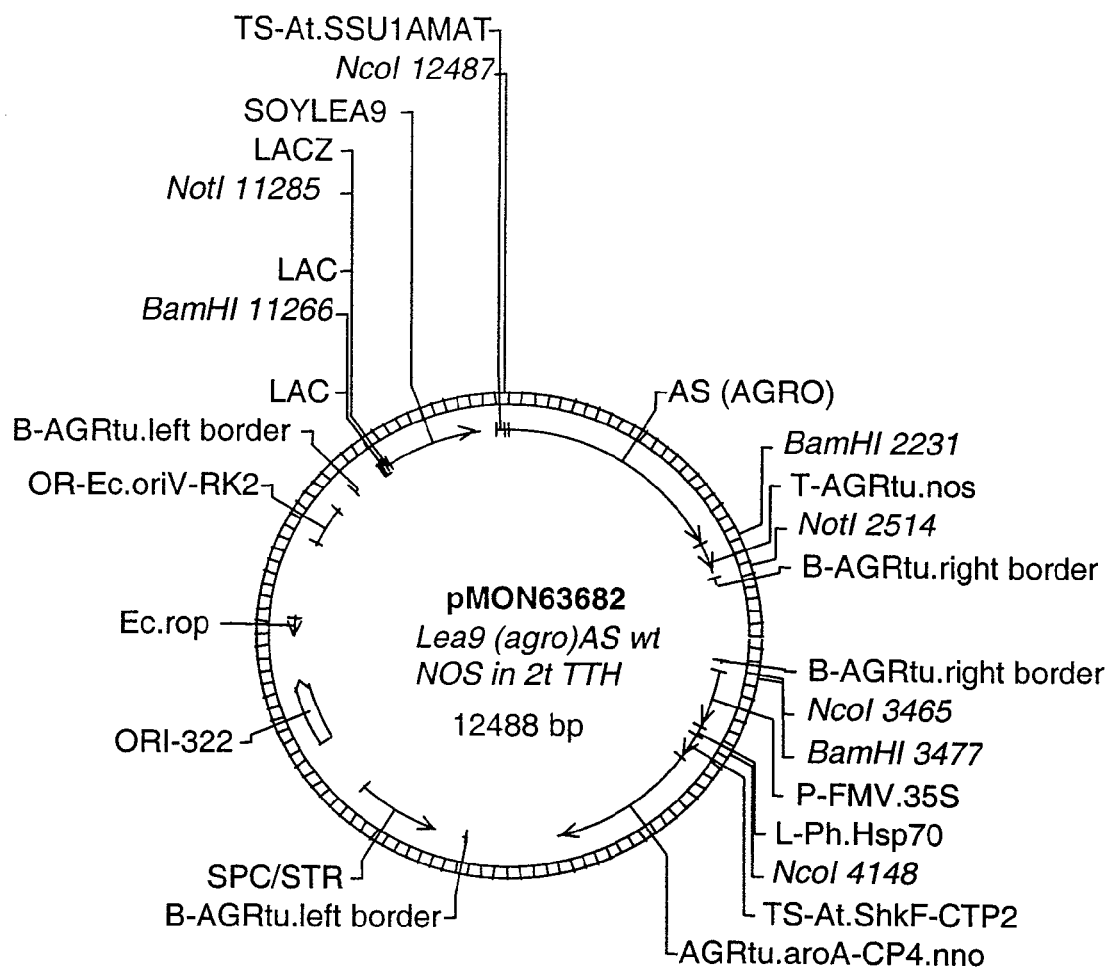
FIG. 13 is a schematic representation of pMON63682.

Two *Agrobacterium* transformation vectors are constructed by following standard molecular cloning protocols (Sambrook et al., Molecular Cloning—A laboratory manual, 1989, Cold Spring Harbor Laboratory Press; Maliga et al., Methods in Plant Molecular Biology—A laboratory course manual, 1995, Cold Spring Harbor Laboratory Press). An expression cassette consisting of FMV:Elf1α promoter, CTP2 and CP4 coding gene and E9 3'UTR is included as selectable marker in two of the vectors, pMON66893 (FIG. 10), and pMON66894 (FIG. 11). The third vector pMON63682 (FIG. 13) uses an expression cassette consisting of FMV promoter, CTP2 and CP4 coding gene and E9 3'UTR for a selectable marker. In pMON66893 (FIG. 10), the lectin promoter is ligated upstream of a gene consisting of chloroplast transit peptide CTP1 and an *agrobacterium* anthranilate synthase (AgroAS). A NOS 3' UTR is used to signal transcription termination and polyadenylation. Vector pMON66894 (FIG. 11) is constructed similarly to pMON66893, except that the sle2 promoter is used in place of the lectin promoter. Vector pMON63682 (FIG. 13) is also constructed similarly to pMON66893, except that the Lea9 promoter is used in place of the lectin promoter.

*Agrobacterium tumefaciens* Mediated Transformation of Soybeans

The vectors described above are transferred into *Agrobacterium tumefaciens*, strain ABI by a triparental mating method (Ditta et al., *Proc. Natl. Acad. Sci.*, 77:7347-7351 (1980)). The bacterial cells are prepared for transformation by methods well known in the art.

Commercially available soybean seeds (Asgrow A3244) are germinated over a 10-12 hour period. The meristem explants are excised and placed in a wounding vessel and wounded by sonication. Following wounding, the *Agrobacterium* culture described above is added and the explants are incubated in for approximately one hour. Following inoculation, the *Agrobacterium* culture is removed by pipetting and the explants are placed in co-culture for 2-4 days. The explants are then transferred to selection media consisting of Woody Plant Medium (McCown and Lloyd, *Proc. International Plant Propagation Soc.*, 30:421, (1981)), plus 75 μM glyphosate and antibiotics to control Agro overgrowth) for 5-7 weeks to allow selection and growth of transgenic shoots. Phenotype positive shoots are harvested approximately 5-7 weeks post inoculation and placed into selective rooting media comprising Bean Rooting Media (BRM) with 25 μM glyphosate (Martinell, et al., U.S. Pat. No. 5,914,451) for 2-3 weeks. Shoots producing roots are transferred to the greenhouse and potted in soil. Shoots that remain healthy on selection, but do not produce roots are transferred to non-selective rooting media (i.e., BRM without glyphosate) for an additional two weeks. Roots from any shoots that produce roots off selection are tested for expression of the plant selectable marker before they are transferred to the greenhouse and potted in soil. Plants are maintained under standard greenhouse conditions until R1 seed harvest.

Free Amino Acid Analysis

The levels of free amino acids are analyzed from each of the transgenic events using the following procedure. Seeds from each of the transgenic events are crushed individually into a fine powder and approximately 50 mg of the resulting powder is transferred to a pre-weighed centrifuge tube. The exact sample weight of the sample is recorded and 1.0 ml of 5% trichloroacetic acid is added to each sample tube. The samples are mixed at room temperature by vortex and then centrifuged for 15 minutes at 14,000 rpm on an Eppendorf microcentrifuge (Model 5415C, Brinkmann Instrument, Westbury, N.Y.). An aliquot of the supernatant is removed and analyzed by HPLC (Agilent 1100) using the procedure set forth in Agilent Technical Publication "Amino Acid Analysis Using the Zorbax Eclipse-AAA Columns and the Agilent 1100 HPLC," Mar. 17, 2000.

The results indicate that transformed soybeans, which have the AgroAS gene driven by the lea9, Lectin and the sle2 promoters, have higher levels of free tryptophan in their seeds.

Example 6

This example describes the analysis of gene expression under the control of the lea9 and per1 promoters in transformed soybean plants, to test the effectiveness of the lea9 and per1 promoters in driving heterologous genes in transgenic soybean plants resulting in elevated levels of amino acids in the seeds.

Vector Construction

Figure 6:
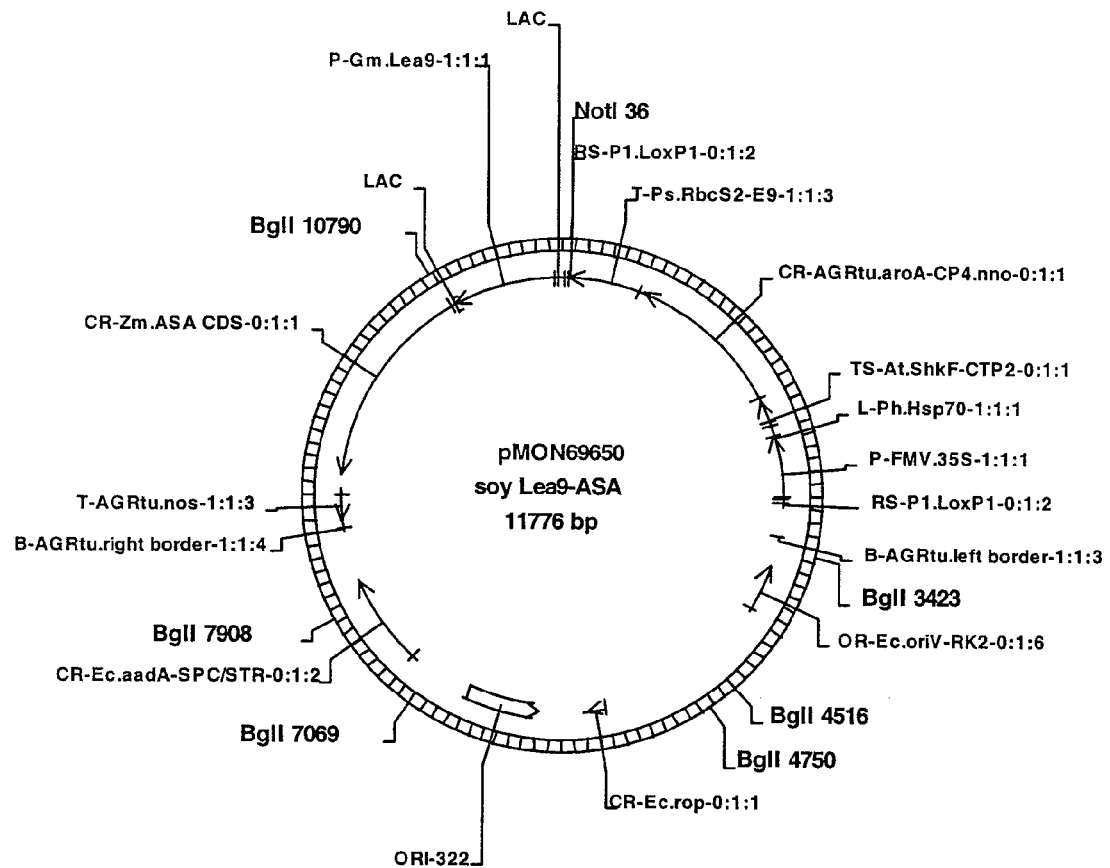
FIG. 6 is a schematic representation of pMON69650.
Figure 7:
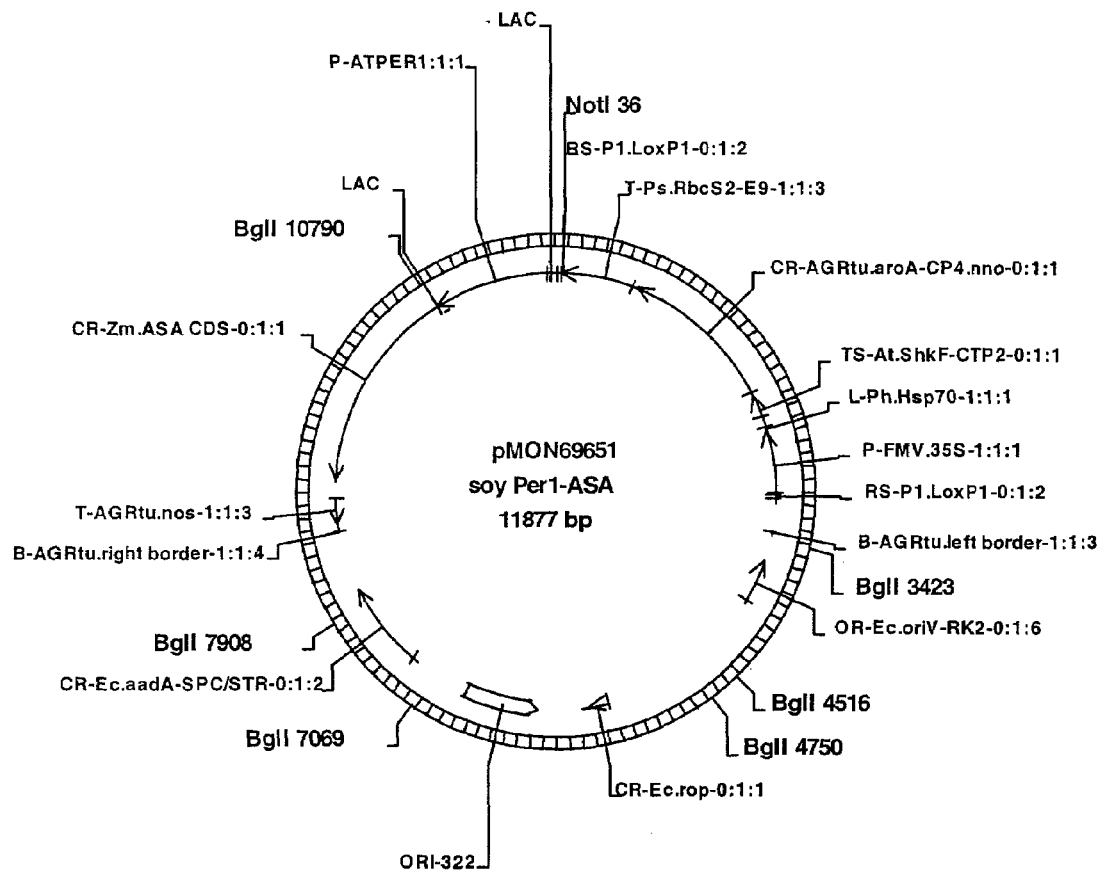
FIG. 7 is a schematic representation of pMON69651.
Figure 12:
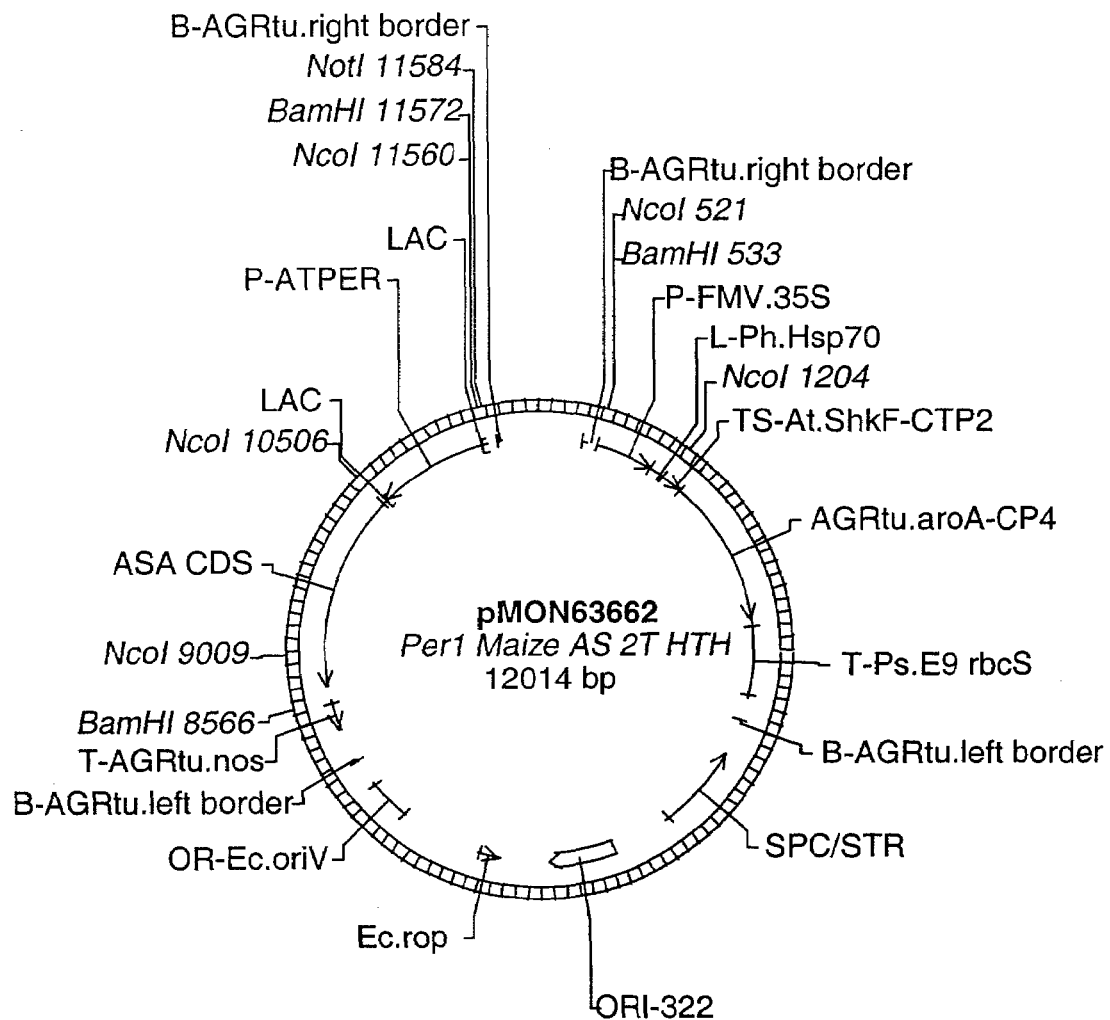
FIG. 12 is a schematic representation of pMON63662.

Four *Agrobacterium* transformation vectors are constructed by following standard molecular cloning protocols (Sambrook et al., Molecular Cloning—A laboratory manual, 1989, Cold Spring Harbor Laboratory Press; Maliga et al., Methods in Plant Molecular Biology—A laboratory course manual, 1995, Cold Spring Harbor Laboratory Press). An expression cassette consisting of FMV promoter (with HSP70 Leader sequence), CTP2 and CP4 coding gene and E9 3' UTR is included as selectable marker in all four vectors. In pMON69650 (FIG. 6), the lea9 promoter is ligated upstream of a tryptophan-insensitive α-subunit of anthranilate synthase from C28 maize (Anderson et al., U.S. Pat. No. 6,118,047). A NOS 3' UTR is used to signal transcription termination and polyadenylation. Vector pMON69651 (FIG. 7) is constructed similarly to pMON69650, except that the per1 promoter is used in place of lea9, driving the same tryptophan-insensitive α-subunit of anthranilate synthase from C28 maize. Vector pMON63662 (FIG. 12) contains the same genetic elements as pMON69651, except that two sets of borders are used to separate the gene of interest and the selectable marker, allowing for independent segregation of the marker and anthranilate synthase genes.

Figure 8:
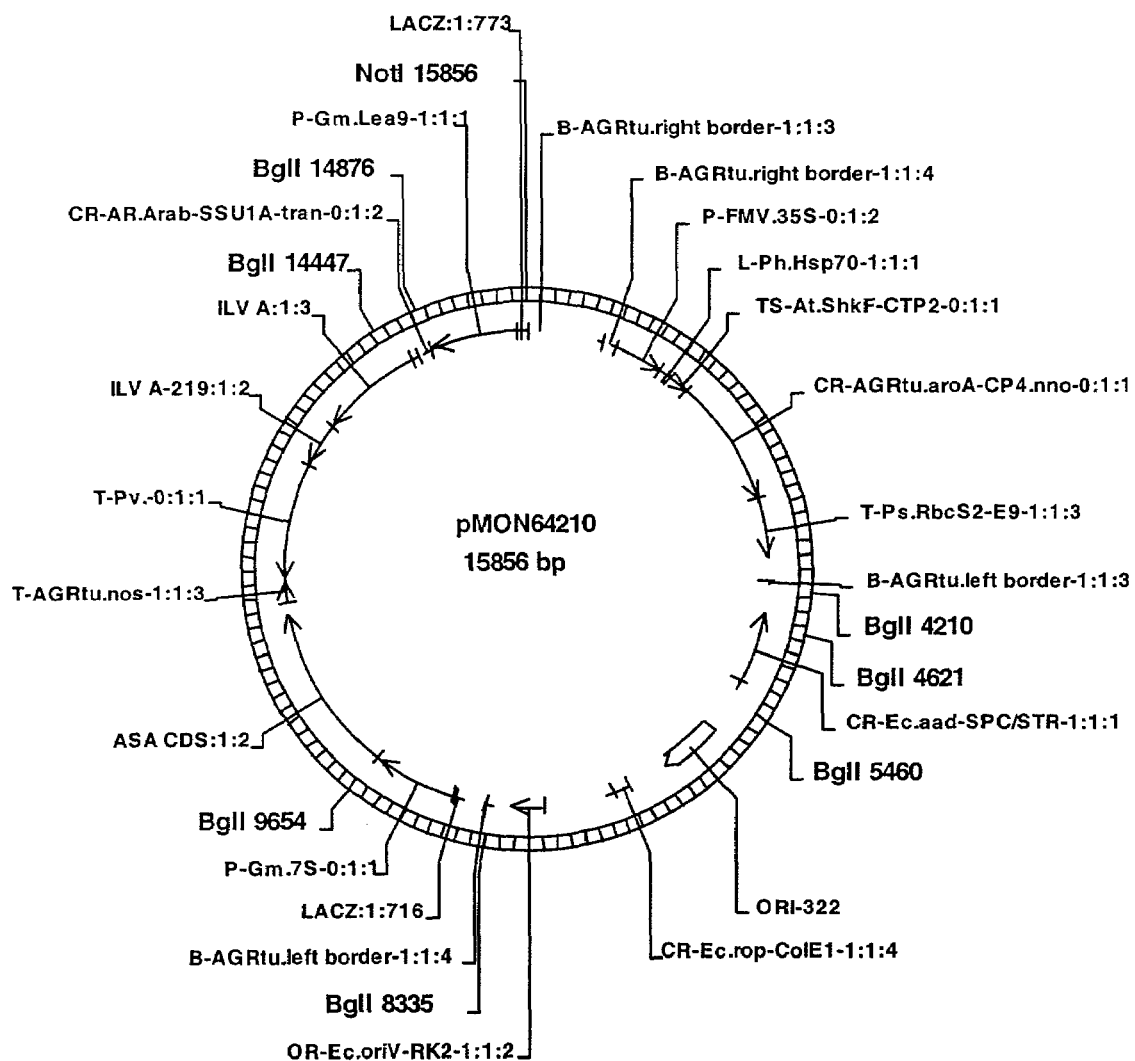
FIG. 8 is a schematic representation of pMON64210.
Figure 9:
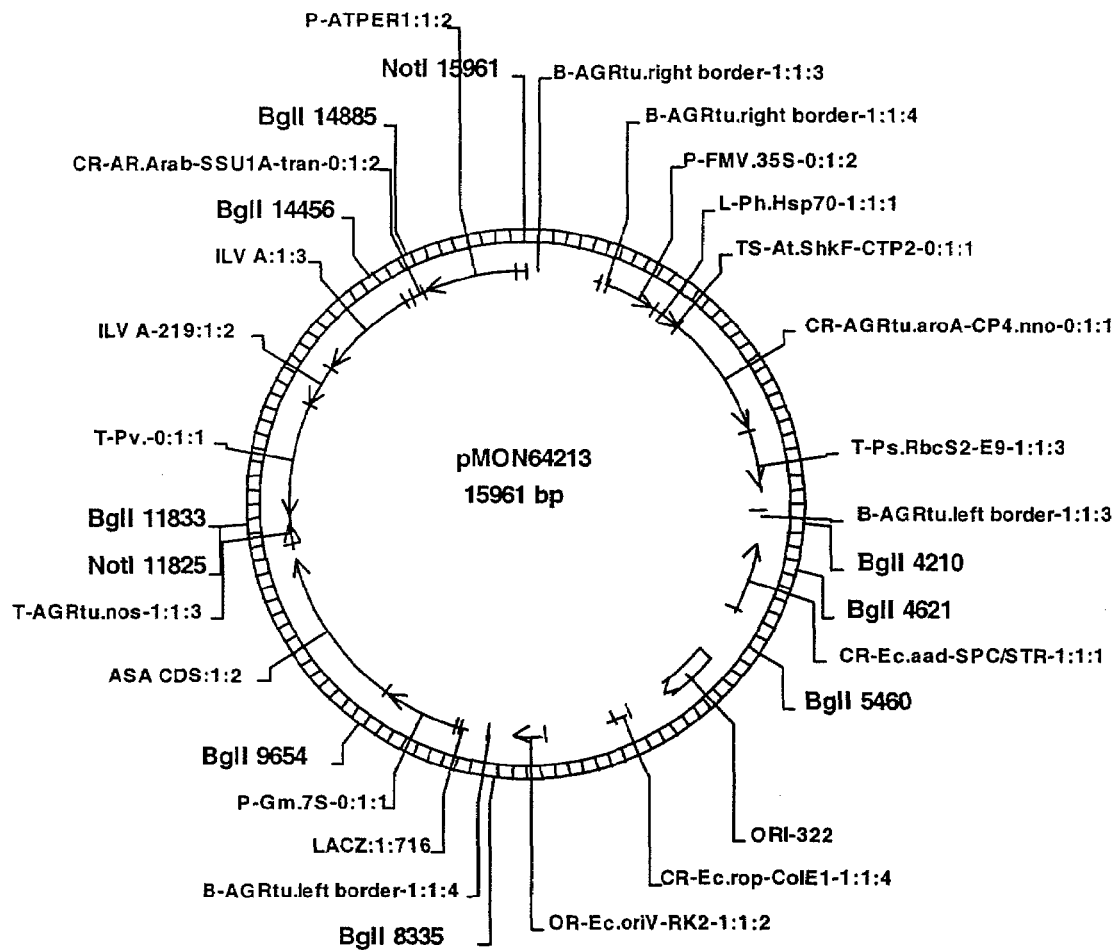
FIG. 9 is a schematic representation of pMON64213.

The vectors pMON64210 (FIG. 8) and pMON64213 (FIG. 9) are designed to demonstrate simultaneous deregulation of multiple pathways. Both pMON64210 and pMON64213 contain a 7Sα' promoter driving the tryptophan-insensitive α-subunit of anthranilate synthase from C28 maize, with the NOS 3' UTR. Additionally, pMON64210 contains an expression cassette consisting of a lea9 promoter driving a fusion protein of *Arabidopsis* SSU CTP and an Ile-insensitive threonine deaminase (Gruys et al., U.S. Pat. No. 5,942,660) with Arc5 3' UTR. The vector pMON64213 is constructed similarly to pMON64210 except per1 promoter is used in place of lea9, driving the same tryptophan-insensitive α-subunit of anthranilate synthase from C28 maize.

*Agrobacterium tumefaciens* Mediated Transformation of Soybeans

The vectors described above are transferred into *Agrobacterium tumefaciens*, strain ABI by a triparental mating method (Ditta et al., Proc. Natl. Acad. Sci., 77:7347-7351 (1980)). The bacterial cells are prepared for transformation by methods well known in the art.

Commercially available soybean seeds (Asgrow A3244) are germinated over a 10-12 hour period. The meristem explants are excised and placed in a wounding vessel and wounded by sonication. Following wounding, the *Agrobacterium* culture described above is added and the explants are incubated in for approximately one hour. Following inoculation, the *Agrobacterium* culture is removed by pipetting and the explants are placed in co-culture for 2-4 days. The explants are then transferred to selection media consisting of Woody Plant Medium (McCown and Lloyd, Proc. *International Plant Propagation Soc.*, 30:421, (1981)), plus 75 µM glyphosate and antibiotics to control Agro overgrowth) for 5-7 weeks to allow selection and growth of transgenic shoots. Phenotype positive shoots are harvested approximately 5-7 weeks post inoculation and placed into selective rooting media comprising Bean Rooting Media (BRM) with 25 µM glyphosate (Martinell, et al., U.S. Pat. No. 5,914,451) for 2-3 weeks. Shoots producing roots are transferred to the greenhouse and potted in soil. Shoots that remain healthy on selection, but do not produce roots are transferred to non-selective rooting media (i.e., BRM without glyphosate) for an additional 2 weeks. Roots from any shoots that produce roots off selection are tested for expression of the plant selectable marker before they are transferred to the greenhouse and potted in soil. Plants are maintained under standard greenhouse conditions until R1 seed harvest.

Free Amino Acid Analysis

The levels of free amino acids are analyzed from each of the transgenic events using the following procedure. Seeds from each of the transgenic events are crushed individually into a fine powder and approximately 50 mg of the resulting powder is transferred to a pre-weighed centrifuge tube. The exact sample weight of the sample is recorded and 1.0 ml of 5% trichloroacetic acid is added to each sample tube. The samples are mixed at room temperature by vortex and then centrifuged for 15 minutes at 14,000 rpm on an Eppendorf microcentrifuge (Model 5415C, Brinkmann Instrument, Westbury, N.Y.). An aliquot of the supernatant is removed and analyzed by HPLC (Agilent 1100) using the procedure set forth in Agilent Technical Publication "Amino Acid Analysis Using the Zorbax Eclipse-AAA Columns and the Agilent 1100 HPLC," Mar. 17, 2000.

The data from this analysis is shown in the tables below. Because the R1 seeds from each event represent a population of segregating seeds, the seed with the highest tryptophan level among the 10 seeds analyzed per event is chosen as a representative of a homozygous genotype. Ten randomly selected non-transgenic seeds from Asgrow A3244 are also analyzed. The seed with the highest tryptophan level is chosen as the negative control. The data indicate that an increase in tryptophan levels is observed when the lea9 and per1 promoters are driving the expression of the maize ASα gene (pMON69650 and pMON69651, respectively). Both tryptophan and isoleucine levels are increased in transformed plants having the lea9 and per1 promoters drivers the TD gene, (pMON64210 and pMON64213, respectively).

Tryptophan Accumulation in Transgenic Soybean Seeds using pMON69650

| Event No. | Trp (ppm) |
|---|---|
| A3244 | 307 |
| pMON69650- 1 | 3548 |
| 2 | 2339 |
| 3 | 990 |
| 4 | 2983 |
| 5 | 2455 |
| 6 | 2761 |
| 7 | 2720 |
| 8 | 3949 |
| 9 | 1865 |
| 10 | 407 |
| 11 | 2880 |
| 12 | 2062 |
| 13 | 3170 |
| 14 | 3504 |
| 15 | 1723 |
| 16 | 1260 |
| 17 | 708 |
| 18 | 1878 |
| 19 | 1490 |
| 20 | 2437 |
| 21 | 7160 |
| 22 | 2792 |
| 23 | 1292 |
| 24 | 2333 |
| 25 | 696 |
| 26 | 1513 |
| 27 | 2390 |
| 28 | 3636 |
| 29 | 871 |
| 30 | 433 |
| 31 | 2122 |
| 32 | 2116 |
| 33 | 665 |
| 34 | 435 |

Tryptophan Accumulation in Transgeneic Soybean Seeds using pMON69651

| Event No. | Trp(ppm) |
|---|---|
| A3244 | 307 |
| pMON69651-1 | 3249 |
| 2 | 3284 |
| 3 | 4649 |
| 4 | 2808 |
| 5 | 3832 |
| 6 | 2264 |
| 7 | 4400 |
| 8 | 2854 |
| 9 | 5160 |
| 10 | 5479 |
| 11 | 2647 |
| 12 | 4079 |
| 13 | 2994 |
| 14 | 3946 |
| 15 | 5511 |
| 16 | 515 |
| 17 | 958 |
| 18 | 2764 |

Tryptophan and Isoleucine Accumulation in Transgenic Soybean Seeds using pMON64210

| Event No. | ILE(ppm) | TRP(ppm) |
|---|---|---|
| A3244 | 182.4 | 86.9 |
| pMON64210-1 | 8829.6 | 774.7 |
| 2 | 14933.3 | 1763.3 |
| 3 | 21474.8 | 1928.1 |
| 4 | 21892.9 | 2500.0 |
| 5 | 21117.8 | 2489.4 |
| 6 | 20639.7 | 2451.2 |
| 7 | 1843.1 | 347.8 |
| 8 | 19124.1 | 1755.5 |
| 9 | 10000.0 | 1395.5 |
| 10 | 15728.8 | 1305.1 |
| 11 | 21992.6 | 1988.9 |
| 12 | 17530.9 | 2034.0 |

Tryptophan and Isoleucine Accumulation in Transgenic Soybean Seeds using pMON64213

| Event No. | ILE(ppm) | TRP(ppm) |
|---|---|---|
| A3244 | 182.4 | 86.9 |
| pMON64210-1 | 8829.6 | 774.7 |
| 2 | 14933.3 | 1763.3 |
| 3 | 21474.8 | 1928.1 |
| 4 | 21892.9 | 2500.0 |
| 5 | 21117.8 | 2489.4 |
| 6 | 20639.7 | 2451.2 |
| 7 | 1843.1 | 347.8 |
| 8 | 19124.1 | 1755.5 |
| 9 | 10000.0 | 1395.5 |
| 10 | 15728.8 | 1305.1 |
| 11 | 21992.6 | 1988.9 |
| 12 | 17530.9 | 2034.0 |

Trp Levels in Three Marker Free Carrying Per1-Maize AS from pMON63662

| Construct | Event | Line No | Average/event | MaxTrp |
|---|---|---|---|---|
| pMON63662 | GM_A29574 | 28 | 1076 | 1723 |
| pMON63662 | GM_A29578 | 44 | 2129 | 3837 |
| pMON63662 | GM_A29672 | 76 | 1188 | 1549 |

Trp Levels in Three Marker Free (Two Positive and a Null) Lines Carrying Lea9-wt-Agro AS from pMON63682

| Construct | Pedigree | Event | Avg(trp > 450) | MaxTrp |
|---|---|---|---|---|
| pMON63682 | GM_A30383:@.0030. | GM_A30383 | 1678 | 2,018 |
| pMON63682 | GM_A30383:@.0043. | GM_A30383 | 2064 | 2,820 |
| pMON63682 | GM_A30383:@.0084. | GM_A30383 | 0 | 46 |

REFERENCES

Ainley et al., *Plant Mol. Biol.*, 14:949, 1990.
Ausubel et al., *Current Protocols in Molecular Biology*, John Wiley and Sons, Inc., 1995.
Bartley and Scolnik, *Plant Physiol.*, 104:1469-1470, 1994.
Back et al., *Plant Mol. Biol.*, 17:9, 1991.
Bauer et al., *Gene*, 37:73, 1985.
Becker and Guarente, In: Abelson and Simon (eds.), *Guide to Yeast Genetics and Molecular Biology, Methods Enzymol.*, 194:182-187, Academic Press, Inc., NY.
Bennett and LaSure (eds.), *More Gene Manipulations in Fungi*, Academic Press, California, 1991.
Bergeron et al., *TIBS*, 19:124-128, 1994.
Bustos et al., *EMBO J.*, 10:1469-1479, 1991.
Castresana et al., *EMBO J.*, 7:1929-1936, 1988.
Capecchi, *Cell*, 22(2):479-488, 1980.
Cerda-Olmedo et al., *J. Mol. Biol.*, 33:705-719, 1968.
Chau et al., *Science*, 244:174-181. 1989.
Christensen et al., *Plant Mol. Biol.*, 18:675-689, 1992.
Clapp, *Clin. Perinatol.*, 20(1):155-168, 1993.
Costa et al., *Methods Mol. Biol.*, 57:31-44, 1996.
Craik, *BioTechniques*, 3:12-19, 1985.
Craig, *Science*, 260:1902-1903, 1993.
Curiel et al., *Hum. Gen. Ther.*, 3(2):147-154, 1992.
Cyanobase, http://www.kazusa.or.jp/cyanobase.
Dellaporta et al., Stadler Symposium, 11:263-282, 1988.
Demolder et al., *J. Biotechnology*, 32:179-189, 1994.
Deng and Nickloff, *Anal. Biochem.*, 200:81, 1992.
D'Halluin et al., *Bio/Technology*, 10:309-314, 1992.
Doyle et al., *J. Biol. Chem.*, 261:9228-9238, 1986.
Eglitis and Anderson, *Biotechniques*, 6(7):608-614, 1988.
Enderlin and Ogrydziak, *Yeast*, 10:67-79, 1994.
Feinbaum et al., *Mol. Gen. Genet.*, 226:449-456, 1991.
Fraley et al., *Proc. Natl. Acad. Sci. (U.S.A.)*, 80:4803, 1983.
Frits Eckstein et al., *Nucleic Acids Research*, 10:6487-6497, 1982.
Fromm et al., *Proc. Natl. Acad. Sci. (U.S.A.)*, 82(17):5824-5828, 1985.
Fromm et al., *Bio/Technology*, 8:833, 1990.
Fuller et al., *Proc. Natl. Acad. Sci. (U.S.)*, 86:1434-1438, 1989.
Fynan et al., *Proc. Natl. Acad. Sci. (U.S.)*, 90(24):11478-11482, 1993.
Gething and Sambrook, *Nature*, 355:33-45, 1992.
Glick et al., Methods in Plant Molecular Biology and Biotechnology, CRC Press, Boca Raton, Fla., 1993.
Graham and Van der Eb, *Virology*, 54(2):536-539, 1973.
Greener et al., *Mol. Biotechnol.*, 7:189-195, 1997.
Hartl et al., *TIBS*, 19:20-25, 1994.
Hershey and Stoner, *Plant Mol. Biol.*, 17:679-690, 1991.
Hess, *Intern Rev. Cytol.*, 107:367, 1987.
Hinchee et al., *Bio/Technology*, 6:915-922, 1988.
Hinnen et al., *Proc. Natl. Acad. Sci. (U.S.A.)*, 75:1920, 1978.
Horsch et al., *Science*, 227:1229-1231, 1985.
Ikatu et al., *Bio/Technol.*, 8:241-242, 1990.
Jarai and Buxton, *Current Genetics*, 26:2238-2244, 1994.
Jefferson (I), *Plant Mol. Biol, Rep.*, 5:387-405, 1987.
Jefferson (II) et al., *EMBO J*, 6:3901-3907, 1987.
Johnston and Tang, *Methods Cell Biol.*, 43(A):353-365, 1994.
Jones et al., *Science*, 266:789-793, 1994.
Jones et al., *Mol. Gen. Genet.*, 1987.
Julius et al., *Cell*, 32:839-852, 1983.
Julius et al., *Cell*, 37:1075-1089, 1984.
Kares et al., *Plant Mol. Biol.*, 15:905, 1990.
Katz et al., *J. Gen. Microbiol.*, 129:2703-2714, 1983.
Keegstra, *Cell*, 56(2):247-253, 1989.
Keller et al., *EMBO L.*, 8:1309-1314, 1989.
Knutzon et al., *Proc. Natl. Acad. Sci. (U.S.A.)*, 89:2624-2628, 1992.
Kridl et al, *Seed Sci. Res.*, 1:209, 1991.
Kudla et al., *EMBO*, 9:1355-1364, 1990.
Kuhlemeier et al., *Seeds*, 1:471, 1989.
Kunkel, *Proc. Natl. Acad. Sci. (U.S.A.)*, 82:488-492, 1985.
Kyte and Doolittle, *J. Mol. Biol.*, 157:105-132, 1982.
Lam and Chua, *J. Biol. Chem.*, 266:17131-17135, 1990.
Lam and Chua, *Science*, 248:471, 1991.
Lipman and Pearson, *Science*, 227:1435-1441, 1985.
Lindstrom et al., *Developmental Genetics*, 11: 160, 1990.
Lois et al., *Proc. Natl. Acad. Sci. (U.S.)*, 95(5):2105-2110, 1998.
Lu et al., *J. Exp. Med.*, 178(6):2089-2096, 1993.
Luo et al., *Plant Mol. Biol. Reporter*, 6:165, 1988.
MacKenzie et al., *Journal of Gen. Microbiol.*, 139:2295-2307, 1993.
Malardier et al., *Gene*, 78:147-156, 1989.
Mandel et al., *Plant Mol. Biol.*, 29:995-1004, 1995.
McElroy et al., *Seeds*, 2:163-171, 1990.
Nawrath et al., *Proc. Natl. Acad. Sci. (U.S.A.)*, 91:12760-12764, 1994.
Needleman and Wunsch, *Journal of Molecular Biology*, 48:443-453, 1970.
Neuhaus et al., *Theor. Appl. Genet.*, 75:30, 1987.
Odell et al., *Nature*, 313:810, 1985.
Osuna et al., *Critical Reviews In Microbiology*, 20:107-116, 1994.
Ou-Lee et al., *Proc. Natl. Acad. Sci. (U.S.A.)*, 83:6815, 1986.
Ow et al., *Science*, 234:856-859, 1986.
Pearson and Lipman, *Proc. Natl. Acad. Sci. (U.S.A.)*, 85:2444-2448, 1988.
Pearson, "Rapid and Sensitive Sequence Comparison with FASTP and FASTA." In *Methods in Enzymology*, (R. Doolittle, ed.), 183:63-98, Academic Press, San Diego, Calif., 1990.
Pearson, *Protein Science*, 4:1145-1160, 1995.
Pena et al., *Nature*, 325:274, 1987.
Poszkowski et al., *EMBO J*, 3:2719, 1989.

Potrykus et al., *Ann. Rev. Plant Physiol. Plant Mol. Biol.*, 42:205, 1991.
Potrykus et al., *Mol. Gen. Genet.*, 199:183-188, 1985.
Puig and Gilbert, *J. Biol. Chem.*, 269:7764-7771, 1994.
Pyee et al., *Plant J.*, 7:49-59, 1995.
Reynaerts et al., Selectable and Screenable Markers. In Gelvin and Schilperoort. Plant Molecular Biology Manual, Kluwer, Dordrecht, 1988.
Richins et al., *Nucleic Acids Res.*, 20:8451, 1987.
Robinson et al., *Bio/Technology*, 1:381-384, 1994.
Rodriguez et al. Vectors: A Survey of Molecular Cloning Vectors and Their Uses, Butterworths, Boston, 1988.
Rogan and Bessman, *J. Bacteriol.*, 103:622-633, 1970.
Rogers et al., *Meth. In Enzymol.*, 153:253-277, 1987.
Saint Guily et al., *Plant Physiol.*, 100(2):1069-1071, 1992.
Samac et al., *Seeds*, 3:1063-1072, 1991.
Sambrook et al., *Molecular Cloning: A Laboratory Manual*, Second Edition, Cold Spring Harbor Laboratory Press, Cold Spring Harbor, N.Y., 1989.
Sato et al., *J. DNA Res.*, 7(1):31-63, 2000.
Schulze-Lefert et al., *EMBO J.*, 8:651, 1989.
Simpson, *Science*, 233:34, 1986.
Singer and Kusmierek, *Ann. Rev. Biochem.*, 52:655-693, 1982.
Slighton and Beachy, *Planta*, 172:356, 1987.
Smith et al., In: *Genetic Engineering: Principles and Methods*, Setlow et al., Eds., Plenum Press, NY, 1-32, 1981.
Smith and Waterman, *Advances in Applied Mathematics*, 2:482-489, 1981.
Smith et al., *Nucleic Acids Research*, 11:2205-2220, 1983.
Smith et al., *Plant J*, 11:83-92, 1997.
Stalker et al., *J. Biol. Chem.*, 263:6310-6314, 1988.
Sutcliffe et al., *Proc. Natl. Acad. Sci. (U.S.A.)*, 75:3737-3741, 1978.
Takahashi et al., *Proc. Natl. Acad. Sci.* (U.S.), 951(17):9879-9884, 1998.
Thillet et al, *J. Biol. Chem.*, 263:12500-12508, 1988.
Vandeyar et al. *Gene*, 65:129-133, 1988
Van Tunen et al., *EMBO J*, 7:1257, 1988.
Verdier, *Yeast*, 6:271-297, 1990.
Vodkin et al., *Cell*, 34:1023, 1983.
Vogel et al., *J. Cell Biochem.*, *(Suppl)* 13D:312, 1989.
Wagner et al., *Proc. Natl. Acad. Sci. (U.S.A.)*, 89(13):6099-6103, 1992.
Wang and Tsou, *FASEB Journal*, 7:1515-1517, 1993.
Weissbach and Weissbach, *Methods for Plant Molecular Biology*, (Eds.), Academic Press, Inc., San Diego, Calif., 1988.
Weisshaar et al., *EMBO J.*, 10:1777-1786, 1991.
Wenzler et al., *Plant Mol. Biol.*, 12:41-50, 1989.
Williams, et al., *Biotechnology*, 10:540-543, 1992.
Wong and Neumann, *Biochim. Biophys. Res. Commun.*, 107 (2):584-587, 1982.
Xia et al., *J. Gen. Microbiol.*, 138:1309-1316, 1992.
Yang et al., *Proc. Natl. Acad. Sci.* (U.S.), 87:4144-48, 1990.
Yamaguchi-Shinozaki et al., *Plant Mol. Biol.*, 15:905, 1990.
Yelton et al., *Proc. Natl. Acad. Sci.* (U.S.), 81:1470-1474, 1984.
Zhou et al., *Methods in Enzymology*, 101:433, 1983.
Zukowsky et al., *Proc. Natl. Acad. Sci. (U.S.A.)*, 80:1101-1105, 1983.
U.S. Pat. Nos. 4,683,195; 4,683,202; 4,757,011; 4,769,061; 4,885,357, 4,886,878, 4,940,835; 4,957,748; 4,971,908; 5,057,419; 5,093,249; 5,100,679; 5,147,792; 5,215,912; 5,219,596; 5,270,200; 5,298,421; 5,304,481; 5,344,771; 5,362,865; 5,576,203; 5,508,468; 5,003,045; 5,955,329; 5,367,110; 5,858,749; 6,040,160; 5,610,041; 5,618,988; 6,107,060; 5,811,636; 4,766,072; 5,003,045; 5,576,203; 5,384,253; 5,443,974; 5,512,482; 5,530,186; 5,534,421; 5,552,306; 5,589,616; 5,508,468; 5,614,393; 5,663,068; 5,663,068; 5,633,436; 5,639,790; 5,654,402; 5,659,645; 5,689,050; 5,689,050; 5,689,052; 5,705,391; 5,760,206; 5,759,829; 5,789,220; 5,807,893; 5,850,024; 5,856,157; 5,866,789; 5,885,802; 5,885,801; 5,914,450; 5,942,660; 5,945,585; 5,952,544; 5,955,650; 5,965,727; 5,995,329; 5,990,384; 5,990,389; 5,936,069; 5,939,599; 6,005,076; 6,051,754; 6,075,183; 6,043,411; 6,100,091; 6,107,051; 6,110,891; 6,117,677; 6,194,167; 6,146,669; 6,147,279; 6,156,227; 6,172,106; and 6,232,122.
European Patents 0 154 204; 0 238 023; and 0 255 378.
Patent Applications WO 90/01869, WO 91/13993, WO 92/14822, WO 93/08682, WO 94/20628, WO 95/19442, WO 97/26366, WO 97/28247, WO 97/22703, WO 98/55601, WO 98/26064, WO 96/17064, WO 97/35023, WO 00/19839, WO 99/06581, WO 99/02656, WO 99/40209, WO 99/11800, WO 99/49058, WO 00/32757, WO 00/10380.

What is claimed is:

1. An isolated nucleic acid molecule comprising a nucleotide sequence having at least 99% identity to SEQ ID NO: 2 or the complement thereof, wherein the nucleotide sequence is capable of directing transcription of an operably linked nucleic acid sequence.

2. A nucleic acid construct comprising a promoter operably linked to a second nucleic acid, wherein the promoter comprises the nucleic acid molecule of claim 1.

3. A plant comprising the nucleic acid construct of claim 2.

4. The plant of claim 3, wherein said second nucleic acid is a structural nucleic acid.

5. The plant of claim 4, wherein said structural nucleic acid encodes a protein selected from the group consisting of a seed storage protein, a fatty acid pathway enzyme, a tocopherol biosynthetic enzyme, an amino acid biosynthetic enzyme, a steroid pathway enzyme, and a starch branching enzyme.

6. The plant of claim 4, wherein said structural nucleic acid encodes a protein selected from the group consisting of anthranilate synthase, tryptophan decarboxylase, threonine deaminase, and aspartate kinase.

7. The plant of claim 4, wherein said structural nucleic acid encodes a starch branching enzyme.

8. The plant of claim 4, wherein said structural nucleic acid is oriented to express an antisense RNA molecule.

9. The plant of claim 3, wherein said plant is selected from the group consisting of canola, crambe, mustard, castor bean, sesame, cottonseed, linseed, maize, soybean, *Arabidopsis phaseolus*, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris, Brassica napus*, turfgrass, sugarbeet, coffee, and dioscorea.

10. The plant of claim 3, wherein said plant is soybean.

11. The plant of claim 4, wherein said structural nucleic acid is expressed in an organ specific manner.

12. The plant of claim 11, wherein said structural nucleic acid is expressed in a seed.

13. A method of producing a transformed plant comprising:
(a) providing the nucleic acid construct of claim 2, wherein said second nucleic acid is a structural nucleic acid; and
(b) transforming a plant with said nucleic acid construct.

14. The method of claim 13, wherein said plant produces a seed and said structural nucleic acid is transcribed in said seed.

15. A meal comprising the plant of claim 12.

16. A feedstock comprising the plant of claim 12.

17. A cell containing the nucleic acid construct of claim 2.

18. The cell according to claim 17, wherein said cell is selected from the group consisting of a bacterial cell, a mammalian cell, an insect cell, a plant cell, and a fungal cell.

19. The cell according to claim 18, wherein said cell is *Agrobacterium tumefaciens*.

20. A seed generated by a plant containing the nucleic acid construct of claim 2.

21. A method for expressing a structural nucleic acid in a plant, comprising:
transforming said plant with a nucleic acid molecule comprising a promoter operably linked to said structural nucleic acid, wherein said promoter comprises the nucleic acid molecule of claim 1,
and wherein said promoter and said structural nucleic acid are heterologous with respect to each other; and
(b) growing said plant.

22. The method of claim 21, wherein said structural nucleic acid is in the anti-sense orientation.

23. A method of accumulating free amino acids in a seed of a plant, comprising:
(a) transforming said plant with the nucleic acid construct of claim 2, wherein the second nucleic acid encodes an amino acid biosynthesis gene, and wherein said promoter and said second nucleic acid are heterologous with respect to each other; and
(b) growing said plant.

24. A method of controlling the germination of a soybean seed, comprising
(a) transforming a plant with the nucleic acid construct of claim 2, wherein the second nucleic acid encodes a gibberellin biosynthetic polypeptide, and wherein said promoter and said second nucleic acid are heterologous with respect to each other;
(b) growing said plant;
(c) harvesting seed from said plant; and
(d) planting said seed.

25. The isolated nucleic acid molecule of claim 1, comprising SEQ ID NO:2.

26. The nucleic acid construct of claim 2, wherein the promoter comprises SEQ ID NO:2.

27. The plant of claim 3, wherein the promoter comprises SEQ ID NO:2.

* * * * *

UNITED STATES PATENT AND TRADEMARK OFFICE
CERTIFICATE OF CORRECTION

PATENT NO. : 7,615,680 B2 Page 1 of 1
APPLICATION NO. : 11/625709
DATED : November 10, 2009
INVENTOR(S) : Wang et al.

It is certified that error appears in the above-identified patent and that said Letters Patent is hereby corrected as shown below:

In claim 21, column 56, line 30, delete "transforming" and insert --(a) transforming--.

Signed and Sealed this

Twenty-ninth Day of December, 2009

David J. Kappos
*Director of the United States Patent and Trademark Office*

SEQUENCE LISTING

```
<160> NUMBER OF SEQ ID NOS: 25

<210> SEQ ID NO 1
<211> LENGTH: 1312
<212> TYPE: DNA
<213> ORGANISM: Glycine max

<400> SEQUENCE: 1
actcaaagtt tattgagttt acttagagtt tataaaattt gttgagaatc tacttagagt      60
ttataaaatt tattaaaagc ctaataaaaa aaatttattc aagagttaat cagttaaatc     120
aagagtttga caaatataat cggtgtcctc taggttcaca cggtgtcact cgagcaacca     180
ttttgtgaac aatcaattca accttcgcaa tccctatcac ggcctattgg gacgactttc     240
gagattcact cataatactc caaggaaaat gacagtgtgg gcgcttaagt gtgataaggt     300
tagtttgggt aattaattaa aaaaaagtta acaccgttat taatcatgat agttaaagag     360
```

```
agatacaaga aatataattt gaaataggaa tatcggtgta ataagtctta atccaagagg      420
aagcgaatat aatttgctca ataaaaaata attgtatcca tatcttttac caagttttat      480
ggagtaaaca attattcagt ctctaacaac tggaagactt tgtgaaaatg tcataaattt      540
ctaaatatca aaaaagatc tagctaacta tttaatgtcg tcatggtccc taaatatcta       600
ttcattttat tacctaaatc acactcttta taaacatttg gactaaggcc actgtctata     660
ttttgtctat ttacatgttc agaaattttg tttgatattt ttttcatttt tcaggataca     720
gcaccatcac tcaaattaaa ttttatgtaa caagtaatca agtaaattaa ttttatgtgt     780
ttcaatatta ttagtgacca tatcaacaca acatgcaact tctccatgca aatgaagtac    840
ctaatttaag taactgcata tgaacgacca aaaacaggtt caactcagca acatagtacc    900
ccaacacgct acagacaacc gcaaccgaga aaccaaaact aatacttgac catgctctag    960
accccacacg tgtcacttgg agagttacag cacctgcgtg tcttctttct cctttagccg   1020
cgtctgtgtt gcacgtgtca atgcatggca acacttactt tttccatttt aacccgtcgt   1080
caccttctgg ttaattccct ctagctaatt acaatgcatg atatatatga tgagttacaa   1140
aacattaatt attattatat gtgaattatg tcacaaattt gttctctata tataccctct   1200
aaccctatct cttcttgtca catagctttg aacacaaaac aaaaagttta cgttacaaat   1260
cgcataataa ccgtcctaaa tttattgaga gaattttgca agtgtgagaa ac            1312

<210> SEQ ID NO 2
<211> LENGTH: 885
<212> TYPE: DNA
<213> ORGANISM: Glycine max

<400> SEQUENCE: 2
caagtactta cgccacacca acttacaaca atgtcataca taaatcatag tgtgacatta      60
ttgcgatttt tgtactgaaa acaatatttt ttaaaatata tgtacgaagg caaagagcta     120
aactttgttg ttctatctct atttcaaatt cttcctttcc atctctcttt tttcttttca     180
attcaccctt cacattctct ttcaattgag gaatggttca acactacgtg cgataggcta     240
aatgtcactt ccactttaat ataaataaag gatcatattt ttgtatcaat tgataaagaa     300
agtttttttt tttcttcatg tttttatctg cctctaacta ctagtaagtg gtattaatta     360
gagcttaagt tgcatagaat taagagaaa catttgagag ttgagagatg attagcaata     420 atttaatca ataatcaata acttttagta tatttcgcat ttgatttaac ttttttattat    480 ccttttcaa attattcttt caaaatgata tcattttaaa tattaataca aatcttaaca    540
tcatatggaa gggataacgg agagacaatt tggaagggat aagagaagtc aatttcatcc    600
ccaattagat taatcgaccg tttatgtaag cccctattgc acgagtggtt gattgccacg    660
tgtccctaac actgtgttga agctcgttgc aaacagacac gcggcaatta cgtgtaagac    720
gattagtcca ataatcctca gaaacttgcc acgcgtactg cactgacacg tgtgcaaaag    780
atagcgccgc acctaaatct atttatttgg tagcatgcgg tgtgctgttg aaagaagaaa    840
gaacctaagt gagaaacaaa gaaaggaaat aattgatctt tgaaa                    885

<210> SEQ ID NO 3
<211> LENGTH: 1006
<212> TYPE: DNA
<213> ORGANISM: Arabidopsis thaliana
```

<400> SEQUENCE: 3

```
taatagactt tgcacctcca tctatatagt atatcacagg acaataaaca caatgatcag      60
tgattataca acatcaaaga aaacttgtaa ttctgggaat ataactgaga atgagaatt      120
aaagattcat aatttgaaca caagaaatcc taaactggta cgaaagaaaa attgctcaac    180
aaaaaaatca agctaattac tcgtatacaa agacacgaag aactaataca agaaacaaga    240
aacaacaaac cacaaagaga ttgaaccaat ccaaattcga caacataaac caagtgtgtg    300
ggtgattgga atcagaggac gtaccaaaga aaagcgtccg tgatcaacaa aaaccaaaaa    360
gagacgtttg aaataaacca gaggaagacg aagaataatt aagcaaagag aagcgttaag    420
cgggagcgag aaaggaaacg agagaaagag agagcttcca gatccgacag aagttttcgg    480
cttcttcttt ttcgtttaag aacttctgat cctcctaggt ctgtccgaag aactaatctt    540
tttgaggtaa cgacgccgtt tttctcaaaa catgggccca ttaaccatag tctcggccca    600
aacgaaactt aatacgacaa tgtttgggtg taaacgcaaa gattttgtcg attatcacaa    660
gtaaaaaaat aaatacaaac acttgagtct ctctagacat cgtgcgtcgc cttagcttta    720
agttttttct cgaaacaaaa gagttatttt atttgaactt tgaagattat acgaagacac    780
gtggcgtgaa cccaattcat aacaacgcca cgctatactc ttttgcatgc acctcaattt    840
gaacatcatc aagtctctct ctctcttttt ctgactttga tccacgaacc taaccagctt    900
gcgatctcta tttaatcggt cctcgacgca acttcaactt ctactacatc cattcacatc    960
aaatcaatac agaaagttttt ttctatatat aaatataaaa ggtaaa                 1006
```

<210> SEQ ID NO 4
<211> LENGTH: 945
<212> TYPE: DNA
<213> ORGANISM: Glycine max

<400> SEQUENCE: 4

```
atggaataca gcaatgaaca aatgctatcc tcttgagaaa agtgaatgca gcagcagcag      60
cagactagag tgctacaaat gcttatcctc ttgagaaaag tgaatgcagc ggcagcagac    120
ctgagtgcta tatacaatta gacacagggt ctattaattg aaattgtctt attattaaat    180
atttcgtttt atattaattt tttaaatttt aattaaattt atatatatta tatttaagac    240
agatatattt atttgtgatt ataaatgtgt cactttttct tttagtccat gtattcttct    300
atttttttcaa tttaactttt tatttttatt tttaagtcac tcctgatcaa gaaaacattg    360
ttgacataaa actattaaca taaaattatg ttaacatgtg ataacatcat attttactaa    420
tataacgtcg cattttaacg tttttttaac aaatatcgac tgtaagagta aaaatgaaat    480
gtttgaaaag gttaattgca tactaactat tttttttcct ataagtaatc ttttttggga    540
tcaattatat atcattgaga tacgatatta aatatgggta cctttccaca aaacctaacc    600
cttgttagtc aaaccacaca taagagagga tggatttaaa ccagtcagca ccgtaagtat    660
atagtgaaga aggctgataa cacactctat tattgttagt acgtacgtat ttcctttttt    720
gtttagtttt tgaatttaat taattaaaat atatatgcta acaacattaa attttaaatt    780
tacgtctaat tatatattgt gatgtataat aaattgtcaa cctttaaaaa ttataaaaga    840
aatattaatt ttgataaaca acttttgaaa agtacccaat aatgctagta taaataggggg    900
catgactccc catgcatcac agtgcaattt agctgaagca aagca                    945
```

<210> SEQ ID NO 5
<211> LENGTH: 38
<212> TYPE: DNA
<213> ORGANISM: Artificial sequence
<220> FEATURE:
<223> OTHER INFORMATION: Synthetic primer

<400> SEQUENCE: 5
acctgcggcc gccaagtact tacgccacac caacttac                    38

<210> SEQ ID NO 6
<211> LENGTH: 25
<212> TYPE: DNA
<213> ORGANISM: Artificial sequence
<220> FEATURE:
<223> OTHER INFORMATION: Synthetic primer

<400> SEQUENCE: 6
gcagctgttt ccttgatgga ctctc                                  25

<210> SEQ ID NO 7
<211> LENGTH: 36
<212> TYPE: DNA
<213> ORGANISM: Artificial sequence
<220> FEATURE:
<223> OTHER INFORMATION: Synthetic primer

<400> SEQUENCE: 7
gaagatctcc tgcaatttca aagatcaatt atttcc                      36

<210> SEQ ID NO 8
<211> LENGTH: 27
<212> TYPE: DNA
<213> ORGANISM: Artificial sequence
<220> FEATURE:
<223> OTHER INFORMATION: Synthetic primer

<400> SEQUENCE: 8
ggatccaaat caaagtttaa tagactt                                27

<210> SEQ ID NO 9
<211> LENGTH: 22
<212> TYPE: DNA
<213> ORGANISM: Artificial sequence
<220> FEATURE:
<223> OTHER INFORMATION: Synthetic primer

<400> SEQUENCE: 9
tctaggttcg gcaccgtgtc tc                                     22

<210> SEQ ID NO 10
<211> LENGTH: 31
<212> TYPE: DNA
<213> ORGANISM: Artificial sequence
<220> FEATURE:
<223> OTHER INFORMATION: Synthetic primer

<400> SEQUENCE: 10
tagcggccgc taatagactt tgcacctcca t                           31

<210> SEQ ID NO 11
<211> LENGTH: 34
<212> TYPE: DNA
<213> ORGANISM: Artificial sequence
<220> FEATURE:
<223> OTHER INFORMATION: Synthetic primer -continued

```
<400> SEQUENCE: 11
aaccatggtt tacctttat atttatatat agaa                                    34

<210> SEQ ID NO 12
<211> LENGTH: 24
<212> TYPE: DNA
<213> ORGANISM: Artificial sequence
<220> FEATURE:
<223> OTHER INFORMATION: Synthetic primer

<400> SEQUENCE: 12
gtaacgcgct ttcccaccaa cgct                                              24

<210> SEQ ID NO 13
<211> LENGTH: 26
<212> TYPE: DNA
<213> ORGANISM: Artificial sequence
<220> FEATURE:
<223> OTHER INFORMATION: Synthetic primer

<400> SEQUENCE: 13
gtgttacatt atcacttatc ctggtc                                            26

<210> SEQ ID NO 14
<211> LENGTH: 25
<212> TYPE: DNA
<213> ORGANISM: Artificial sequence
<220> FEATURE:
<223> OTHER INFORMATION: Synthetic primer

<400> SEQUENCE: 14
gctcaattaa ccctcactaa aggga                                             25

<210> SEQ ID NO 15
<211> LENGTH: 22
<212> TYPE: DNA
<213> ORGANISM: Artificial sequence
<220> FEATURE:
<223> OTHER INFORMATION: Synthetic primer

<400> SEQUENCE: 15
ctcttgagca cgttcttctc ct                                                22

<210> SEQ ID NO 16
<211> LENGTH: 25
<212> TYPE: DNA
<213> ORGANISM: Artificial sequence
<220> FEATURE:
<223> OTHER INFORMATION: Synthetic primer

<400> SEQUENCE: 16
gctcaattaa ccctcactaa aggga                                             25

<210> SEQ ID NO 17
<211> LENGTH: 38
<212> TYPE: DNA
<213> ORGANISM: Artificial sequence
<220> FEATURE:
<223> OTHER INFORMATION: Synthetic primer

<400> SEQUENCE: 17
gtgcggccgc actcaaagtt tattgagttt acttagag                               38
```

<210> SEQ ID NO 18
<211> LENGTH: 34
<212> TYPE: DNA
<213> ORGANISM: Artificial sequence
<220> FEATURE:
<223> OTHER INFORMATION: Synthetic primer

<400> SEQUENCE: 18
acagatctgt ttctcacact tgcaaaattc tctc                            34

<210> SEQ ID NO 19
<211> LENGTH: 20
<212> TYPE: DNA
<213> ORGANISM: Artificial sequence
<220> FEATURE:
<223> OTHER INFORMATION: Synthetic primer

<400> SEQUENCE: 19
atagtacccc aacacgctac                                            20

<210> SEQ ID NO 20
<211> LENGTH: 38
<212> TYPE: DNA
<213> ORGANISM: Artificial sequence
<220> FEATURE:
<223> OTHER INFORMATION: Synthetic primer

<400> SEQUENCE: 20
gtgcggccgc actcaaagtt tattgagttt acttagag                        38

<210> SEQ ID NO 21
<211> LENGTH: 21
<212> TYPE: DNA
<213> ORGANISM: Artificial sequence
<220> FEATURE:
<223> OTHER INFORMATION: Synthetic primer

<400> SEQUENCE: 21
ggaaccgaat ataattggct c                                          21

<210> SEQ ID NO 22
<211> LENGTH: 25
<212> TYPE: DNA
<213> ORGANISM: Artificial sequence
<220> FEATURE:
<223> OTHER INFORMATION: Synthetic primer

<400> SEQUENCE: 22
gccttcctgg tcagtagcac cagta                                      25

<210> SEQ ID NO 23
<211> LENGTH: 25
<212> TYPE: DNA
<213> ORGANISM: Artificial sequence
<220> FEATURE:
<223> OTHER INFORMATION: Synthetic primer

<400> SEQUENCE: 23
ccatgccatc gtatcgtgtc acaat                                      25

<210> SEQ ID NO 24
<211> LENGTH: 41
<212> TYPE: DNA
<213> ORGANISM: Artificial sequence
<220> FEATURE:
<223> OTHER INFORMATION: Synthetic primer -continued

```
<400> SEQUENCE: 24
aggcggccgc ctgcagatgg aatacagcaa tgaacaaatg c                    41

<210> SEQ ID NO 25
<211> LENGTH: 39
<212> TYPE: DNA
<213> ORGANISM: Artificial sequence
<220> FEATURE:
<223> OTHER INFORMATION: Synthetic primer

<400> SEQUENCE: 25
ctccatggag atcttgcttt gcttcagcta aattgcact                       39
```